United States Patent [19]

Daniloff et al.

[11] Patent Number: 5,756,679

[45] Date of Patent: May 26, 1998

[54] DERIVATIZED PYRIDINOLINE REAGENT

[75] Inventors: Yuri Daniloff, Mountain View, Calif.; Simon P. Robins, Aberdeen, Scotland; Brian J. Evans, Santa Clara, Calif.; David A. Pratt, Aberdeen, Scotland; Robert Lungard, Portola Valley, Calif.

[73] Assignee: Metra Biosystems, Inc., Mountain View, Calif.

[21] Appl. No.: 620,418

[22] Filed: Mar. 22, 1996

Related U.S. Application Data

[62] Division of Ser. No. 234,068, Apr. 28, 1994, Pat. No. 5,502,197, which is a division of Ser. No. 954,790, Sep. 30, 1992, Pat. No. 5,350,855.

[51] Int. Cl.[6] .................... C07K 14/765; C07K 14/805; G01N 33/68
[52] U.S. Cl. ............................ 530/363; 530/404; 436/87; 436/88; 546/278.7
[58] Field of Search .................... 530/363, 400, 530/404; 436/87, 88

[56] References Cited

U.S. PATENT DOCUMENTS

| 4,973,666 | 11/1990 | Eyre ........................................ 530/323 |
| 5,350,855 | 9/1994 | Daniloff et al. ........................ 546/291 |

FOREIGN PATENT DOCUMENTS

| WO89/04491 | 5/1989 | WIPO . |
| WO89/12824 | 12/1989 | WIPO . |
| WO91/08478 | 6/1991 | WIPO . |

OTHER PUBLICATIONS

Black, D., et al., "Quantitative Analysis of the Pyridinium Crosslinks of Collagen in Urine Using Ion–Paired Reversed–Phase High–Performance Liquid Chromatography," Anal. Biochem. 169:197–203 (1988).

Black, D., et al., "Urinary excretion of the hydroxypyridinium crosslinks of collagen in patients with rheumatoid arthritis," Ann. Rheumat. Dis. 48:641–644 (1989).

Eyre, D.R., et al., "Quantitation of Hydroxypyridinium Cross–links in Collagen by High–Performance Liquid Chromatography," Anal. Biochem. 137:380–388 (1984).

Fujimoto, D., et al., "Analysis of Pyridinoline, a Cross–Linking Compound of Collagen Fibers, in Human Urine," J. Biochem. 94:1133–1136 (1983).

Hanson, D.A., and Eyre, D.R., "A Specific Immunoassay for Bone Resorption Based on Cross–Linked Collagen Peptides in Urine," Abstract from J. Bone & Mineral Res. 6(1):S251 (1991).

Previero, A., et al., "Specific O–Acylation of Hydroxylamino Acids in Presence of Free Amino Groups," Biochim. Biophys. Acta 263:7–13 (1972).

Robins S. P., et al., "Measurement of the cross linking compound, pyridinoline, in urine as an index of collagen degradation in joint disease," Ann. Rheumat. Dis. 45:969–973 (1986).

Robins, S.P., "An enzyme–linked immunoassay for the collagen cross–link pyridinoline," Biochem. J. 207:617–620 (1982).

Seibel, M.J., et al., "Urinary Hydroxy–pyridinium Crosslinks Provide Indices of Cartilage and Bone Involvement in Arthritic Diseases," J. Rheumatol. 16(7):964–970 (1989).

*Primary Examiner*—Alan L. Rotman
*Attorney, Agent, or Firm*—Vincent M. Powers; Peter J. Dehlinger

[57] ABSTRACT

A pyridinoline composition in which pyridinoline is derivatized specifically at its aliphatic hydroxyl group by a selected chemical group is disclosed. In various embodiments, the composition may be used as a standard for HPLC or immunoassay of pyridinoline, a pyridinoline immunogen for producing anti-pyridinoline antibodies, and a solid-phase reagent for use in an immunoassay kit. Also disclosed are methods for making and using the composition.

8 Claims, 16 Drawing Sheets

XII

1) H⁺, H₂O
2) SOCl₂

XIII

React with Pyd-OH and
HS-Prot as in Fig. 3A

R = (CH₂), (CH₂)₂, (—⌬—CH₂—), etc.

DERIVATIZED PYRIDINOLINE REAGENT

This is a division of application Ser. No. 08/234,068 filed Apr. 28, 1994, now U.S. Pat. No. 5,502,197, which is a division of Ser. No. 07/954,790, filed Sep. 30, 1992, now U.S. Pat. No. 5,350,855.

FIELD OF THE INVENTION

The present invention relates to assays for measuring pyridinoline compounds in a sample, and in particular, to acylated pyridinoline compounds and reagents for use in such assays.

REFERENCES

Black, D., et al., *Anal. Biochem.* 169: 197–203 (1988).

Black, D., et al., *Annals of Rheumatic Diseases* 48: 641–644 (1989).

Brown, J. P., et al., *Lancet* 1091–1093 (1984).

Campbell, A., *Monoclonal Antibody and Immunosensor Technology*, Elsevier (1991).

Cook, J., et al., *Ann. Clin. Biochem.* 12: 219 (1975).

Daniloff, Y., et al., *Connect. Tissue. Res.* 27: 187 (1992).

Eyre, D. R., *J. Clin. Endocrinol. Metab.* 74: 470A–470C (1992).

Eyre, D. R., et al., *Anal. Biochem.* 137: 380–388 (1984).

Eyre, D. R., et al., *FEBS* 2: 337–341 (1987).

Fujimoto, D., et al., *Biochem. and Biophys. Res. Commun.* 76: 1124–1129 (1977).

Fujimoto, D., et al., *J. Biochem.* 83: 863–867 (1978).

Fujimoto, D., et al., *J. Biochem.* 94: 1133–1136 (1983).

Gosling, J., *Clin. Chem.* 36(8): 1408- (1990).

Gunja-Smith, Z., et al., *Biochem. J.* 197: 759–762 (1981).

Harlow, E., et al., *Antibodies: A Laboratory Manual*, Cold Spring Harbor Lab (1988).

Henkel, W., et al., *Eur. J. Biochem.* 165: 427–436 (1987).

Hojo, et al., *Chem. Lett.* 133: 437- (1977).

Macek, J., et al., *Z. Rheumatol.* 46: 237–240 (1987).

Ogawa, T., et al., *Biochem. Biophys. Res. Commun.* 107: 1251–1257 (1982).

Previero, A., et al., *Biochem. Biophys. Acta* 263: 7–13 (1972).

Roberts, J. D., and Caserio, M. C., *Basic Principles of Organic Chemistry*, 2nd Ed., W. A. Benjamin, Inc., Menlo Park, Calif., pp. 308–309 (1977).

Robins, S. P., *Biochem J.* 207: 617–620 (1982a).

Robins, S. P., in *Collagen in Health and Disease* (Weiss, J. B., et al., eds.) pp. 160–178, Churchill Livingstone, Edinburgh (1982b).

Robins, S. P., *Biochem. J.* 215: 167–173 (1983).

Robins, S. P., et al., *Ann. Rheum. Dis.* 45: 969–973 (1986).

Robins, S. P., et al., *Biochim. Biophys. Acta.* 914: 233–239 (1987).

Segel, I., *Biochemical Calculations*, John Wiley and Sons, (1976).

Seibel, et al., *J. Rheumatol* 16: 964–970 (1989).

Wong, S. S., *Chemistry of Protein Conjugation and Cross Linking*, CRC Press, Boca Raton, Fla. (1991).

BACKGROUND OF THE INVENTION

There are a variety of conditions in humans which are characterized by a high level of bone resorption and by an abnormal balance between bone formation and bone resorption. Among the more common of these are osteoporosis, Paget's disease, and conditions related to the progress of benign and malignant tumors of the bone and metastatic cancers which have been transferred to bone cells from, for example, prostate or breast initial tumors. Other conditions which are associated with changes in collagen metabolism include osteomalacial diseases, rickets, abnormal growth in children, renal osteodystrophy, and a drug-induced osteopenia. Irregularities in bone metabolism are often side effects of thyroid treatments and thyroid conditions per se, such as primary hypothyroidism and thyrotoxicosis as well as Cushing's disease.

It has been recognized that disorders of bone resorption or other conditions characterized by an abnormal balance between bone formation and bone resorption can be detected by altered levels of pyridinium crosslinks in urine (Robins, 1982b; Macek; Black). The crosslinks take the form of compounds containing a central 3-hydroxy pyridinium ring in which the ring nitrogen is derived from the epsilon amino group of lysine or hydroxylysine (Fujimoto, 1978; Robins, 1982a; Gunja-Smith; Ogawa; Eyren).

The pyridinium crosslink compounds found in urine can be grouped into four general classes: (1) free, native crosslinks having a molecular weight of about 400 daltons (Fujimoto), (2) glycosylated crosslinks and crosslink peptide forms having a molecular weight of between about 550 and 1,000 daltons (Robins, 1983), (3) crosslink peptide forms having a molecular weight between 1,000 and 3,500 daltons (Robins, 1983, 1984, 1987; Henkel; Eyre), and (4) crosslink peptide forms having a molecular weight greater than 3,500 daltons. In normal adults, these forms account for about 38% (1), 40% (2), 15% (3), and 7% (4) of total urinary crosslinks. About 80% of the free crosslinks in normal adults is pyridinoline (or Pyd), derived from a hydroxylysine residue, and about 20%, deoxypyridinoline, or Dpd, derived from a lysine residue, and this ratio of Pyd/Dpd applies roughly to the other three classes of crosslinks in urine. The higher molecular weight crosslinks can be converted to free crosslinks by acid hydrolysis (Fujimoto, 1978).

Methods for measuring pyridinium crosslinks in urine have been proposed. One of these methods involves the measurement of total hydrolysed Pyd, i.e., Pyd produced by extensive hydrolysis of urinary crosslinks, by quantitating the hydrolysed Pyd peak separated by HPLC (Fujimoto, 1983). The relationship between total hydrolysed Pyd to age was determined by these workers as a ratio to total hydrolysed Pyd/creatinine, where creatinine level is used to normalize crosslink levels to urine concentration and skeletal mass. It was found that this ratio is high in the urine of children, and relatively constant throughout adulthood, increasing slightly in old age. The authors speculate that this may correspond to the loss of bone mass observed in old age.

Studies on the elevated levels of total crosslinks in hydrolyzed urine of patients with rheumatoid arthritis has been suggested as a method to diagnose this disease (Black). The levels of total hydrolyzed crosslinks for patients with rheumatoid arthritis (expressed as a ratio of total crosslinks measured by HPLC to creatinine) were elevated by a factor of 5 as compared to controls. However, only total hydrolysed Pyd, but not total hydrolysed Dpd, showed a measurable increase.

In a more extensive study using hydrolyzed urines, Seibel et al. showed significant increases in the excretion of bone-specific total hydrolysed Pyd crosslinks relative to controls in both rheumatoid and osteoarthritis, but the most marked increases for total hydrolysed Pyd were in patients with rheumatoid arthritis (Seibel).

More recently, the applicants have shown that a variety of bone collagen disorders, including osteoporosis, Paget's disease, osteoarthritis, hyperparathyroidism, and rheumatoid arthritis, can be detected on the basis of characteristic levels of urinary native Pyd or native Dpd. Levels of native Pyd or Dpd were measured by HPLC separation and quantitation of treated urine samples. The use of native crosslinks for detection of these bone disorders is advantageous in that the several-hour hydrolysis step needed to convert pyridinoline crosslinks to hydrolysed Pyd is avoided.

Assay methods, such as those just noted, which involve HPLC quantitation of crosslinks from hydrolysed samples, or crosslink subfractions from non-hydrolysed samples, require accurate calibration of the HPLC peak heights, in order to accurately quantitate each of the peaks. Ideally, an internal standard for use in an HPLC assay of urinary pyridinoline should (a) be recoverable in substantially the same yield as Pyd and Dpd during chromatographic fraction of a urine sample, (b) have similar spectroscopic (e.g. UV-visible absorbance and fluorescence) properties, and (c) be characterized by a retention time close to but distinct from the retention times of Pyd and Dpd in chromatographic analysis (e.g., reversed phase C-18 HPLC).

Immunoassays have also been proposed for measuring urinary crosslinks. U.S. Pat. No. 4,973,666 discloses an assay for measuring bone resorption by detection in urine of specific pyridinium crosslinks, characterized by specific peptide extensions, associated with bone collagen. Two specific entities having peptide extensions presumed to be associated with bone collagen are described. These are obtained from the urine of patients suffering from Paget's disease, a disease known to involve high rates of bone formation and destruction. The assay relies on immunospecific binding of crosslink compounds containing the specific peptide fragment or extension with an antibody prepared against the crosslink peptide. It is not clear whether and how the concentration of crosslink peptide being assayed relates to total urinary crosslinks.

Robins has described a technique for measuring pyridinoline in urine by the use of an antibody specific to hydrolysed Pyd (Robins, 1986). The method has the limitation that the antibody was found to be specific for the hydrolyzed form of Pyd, requiring that the urine sample being tested first be treated under hydrolytic conditions. The hydrolytic treatment increases the time and expense of the assay, and precludes measurements on other native pyridinium crosslinks. More recently, the applicants have disclosed an enzyme immunoassay for detection of native Pyd in urine samples, for use in detecting a variety of bone collagen disorders.

The typical enzyme immunoassay format for detecting Pyd involves a solid-phase reagent containing surface-bound Pyd and a soluble anti-Pyd antibody, where sample Pyd competes with the surface-bound Pyd for binding to the soluble antibody. The extent of binding of antibody to the solid support thus provides a measure of Pyd concentration in the sample. In this format, it is desirable that the surface-bound Pyd resemble free Pyd in its antigenic characteristics, i.e., that its conjugation to the solid surface does not appreciably perturb its reaction affinity for the soluble antibody.

It is also desirable that the anti-Pyd antibody employed in the assay—whether a polyclonal or monoclonal reagent—has a high binding affinity for pyridinoline relative to more complex pyridinoline crosslinks, i.e., crosslinks containing additional glycosylation or peptide moieties, particularly when assaying non-hydrolysed samples. In preparing such an antibody reagent, the immunogen (which is typically a pyridinoline moiety conjugated to a carrier protein) should be relatively unobstructed at its pyridine ring and attached amino acid positions. At the same time, the immunogen should be structurally homogeneous, to reduce the range of antibodies which are produced in response to the immunogen, particularly when the immunogen is used for preparing a polyclonal antibody reagent.

SUMMARY OF THE INVENTION

The present invention includes a pyridinoline composition in which pyridinoline is derivatized specifically at its aliphatic hydroxyl group by a selected chemical group. For use as an internal standard, the derivatized pyridinoline is characterized by a retention time close, to but distinct from, the retention times of pyridinoline and deoxypyridinoline, as determined by reversed phase C-18 liquid chromatography. A preferred chemical group for this embodiment is an acetyl group.

In another embodiment, where the chemical group serves to anchor the pyridinoline to a solid support, the composition is useful in a solid support for an enzyme immunoassay.

In yet another embodiment, where the chemical group serves to anchor the pyridinoline to a carrier protein, the composition is useful for raising antibodies against pyridinium crosslink species. Thus, the invention includes a pyridinoline-protein conjugate having the following structure:

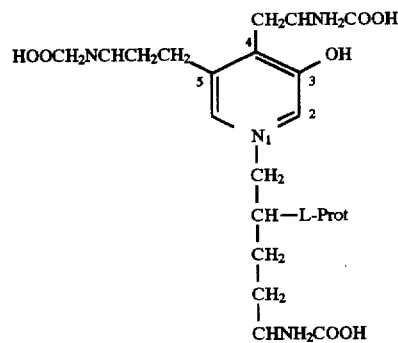

wherein "Prot" is a carrier polypeptide, L is a linker, and the pyridinoline-protein conjugate is effective to serve as an immunogen for raising an antibody specific for the pyridinoline moiety in the conjugate.

In another aspect, the invention includes a method of derivatizing the aliphatic hydroxyl group of pyridinoline. In the method, anhydrous sample of pyridinoline is reacted with an acylating agent in anhydrous trifluoroacetic acid for a time sufficient to selectively derivatize the aliphatic hydroxyl group of the pyridinoline.

In one embodiment, the method is useful for preparing an acylated pyridinoline for use in quantitating pyridinoline in a urine sample.

In another embodiment, the method is useful for preparing a pyridinoline immunogen or a pyridinoline solid-surface reagent for immunoassay applications as above.

Also forming part of the invention is a method of quantitating pyridinoline crosslinks present in a urine sample. The method includes adding to the sample a known quantity of an O-acetylated pyridinoline, resolving the pyridinoline crosslinks and acetylated pyridinoline in the sample by reversed phase C-18 HPLC, and quantitating the separated crosslinks by use of the separated acetylated pyridinoline to calibrate the recovery of the crosslinks.

These and other objects and features of the invention will become more fully apparent when the following detailed description of the invention is read in conjunction with the accompanying drawings.

BRIEF DESCRIPTION OF THE DRAWINGS

In FIG. 6A, the extraction procedure included a wash step with THF. In FIG. 6B, the extraction procedure included a wash step with DMF (same urine sample). FIG. 6C shows baseline resolution of Pyd, Dpd, and Ac-Pyd from an extracted hydrolyzed urine sample.

FIG. 9A shows a reaction of a carrier protein with reagents to produce a thiolated carrier protein. FIG. 9B shows a reaction of a carrier with a bifunctional reagent to produce a carrier protein containing a maleimide group.

DETAILED DESCRIPTION OF THE INVENTION

I. Definitions

"Pyd", "Pyd-OH", "pyridinoline", and "free pyridinoline" refer to the crosslink compound shown at I below, where the ring nitrogen is derived from the θ amino group of a hydroxylysyl residue.

"Dpd", "deoxypyridinoline", and "free deoxypyridinoline" refer to the crosslink compound shown at II below, where the ring nitrogen is derived from the ε amino group of a lysyl residue.

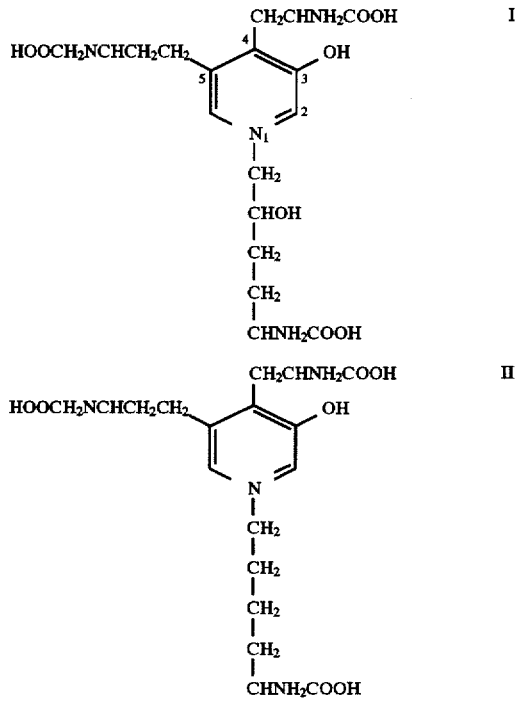

"Free crosslinks" refers to either compounds I or II or a mixture of the two.

"Glycosylated pyridinoline" and "glyco-Pyd" refer to glycosylated forms of compound I.

"Pyd-peptides" and "pyridinoline-peptides" refer to peptide-derivatized forms of compound I, in which one or more of the three amino acid residues in the compound is linked via a peptide linkage to additional amino acid residues.

"Pyd crosslinks" refers to the pyridinium crosslinks in urine which contain compound I either in free or derivatized form. Pyd crosslinks include Pyd, glyco-Pyd and Pyd-peptides. Similarly, "Dpd crosslinks" refers to the pyridinium crosslinks in urine which contain compound II either in free or derivatized form.

"Total H-Pyd" refers to total hydrolysed Pyd produced by hydrolyzing Pyd crosslinks to Pyd. Similarly, "total H-Dpd" refers to total hydrolysed Dpd produced by hydrolyzing Dpd crosslinks to Dpd.

"Hydrolysed-Pyd" and "H-Pyd" refer to Pyd produced by hydrolysing Pyd crosslinks in 6N HCl at 110° C. for ~16–18 hours, or by isolating Pyd from sheep bone by the method of Black et al. (1988). Similarly, "Hydrolysed-Dpd" or "H-Dpd" refers to Dpd produced by hydrolysing Dpd crosslinks in 6N HCl at 110° C. for ~16–18 hours, or by isolating Dpd from sheep bone by the method of Black et al. (1988).

"Hydrolyzed crosslinks" refers to H-Pyd and H-Dpd together.

"Un-hydrolyzed urine" refers to urine samples that were not subjected to hydrolysis conditions.

"Native Pyd" and "N-Pyd" refer to Pyd obtained from urine which has not been subjected to hydrolytic conditions.

Similarly, "Native Dpd" and "N-Dpd" refer to Dpd obtained from urine which has not been subjected to hydrolytic conditions.

"Native crosslinks" refers to N-Pyd and N-Dpd together.

"Pyridinium crosslinks" refers to pyridinium crosslinks which contain compounds I and/or II in free and/or derivatized form.

"Ac-Pyd", "acetylated Pyd", and "O-acetylated Pyd" refer to H-Pyd or N-Pyd that has been acetylated at the aliphatic hydroxyl group, i.e., the lysyl side chain hydroxyl group of Pyd.

"Pr-Pyd", "propionylated Pyd", and "O-propionylated Pyd" refer to H-Pyd or N-Pyd that has been propionylated at the aliphatic hydroxyl group.

"O-acylated Pyd" refers to H-Pyd or N-Pyd that has been acylated at the aliphatic hydroxyl group.

II. Preparation of Acylated Pyridinolines

Figure 1:
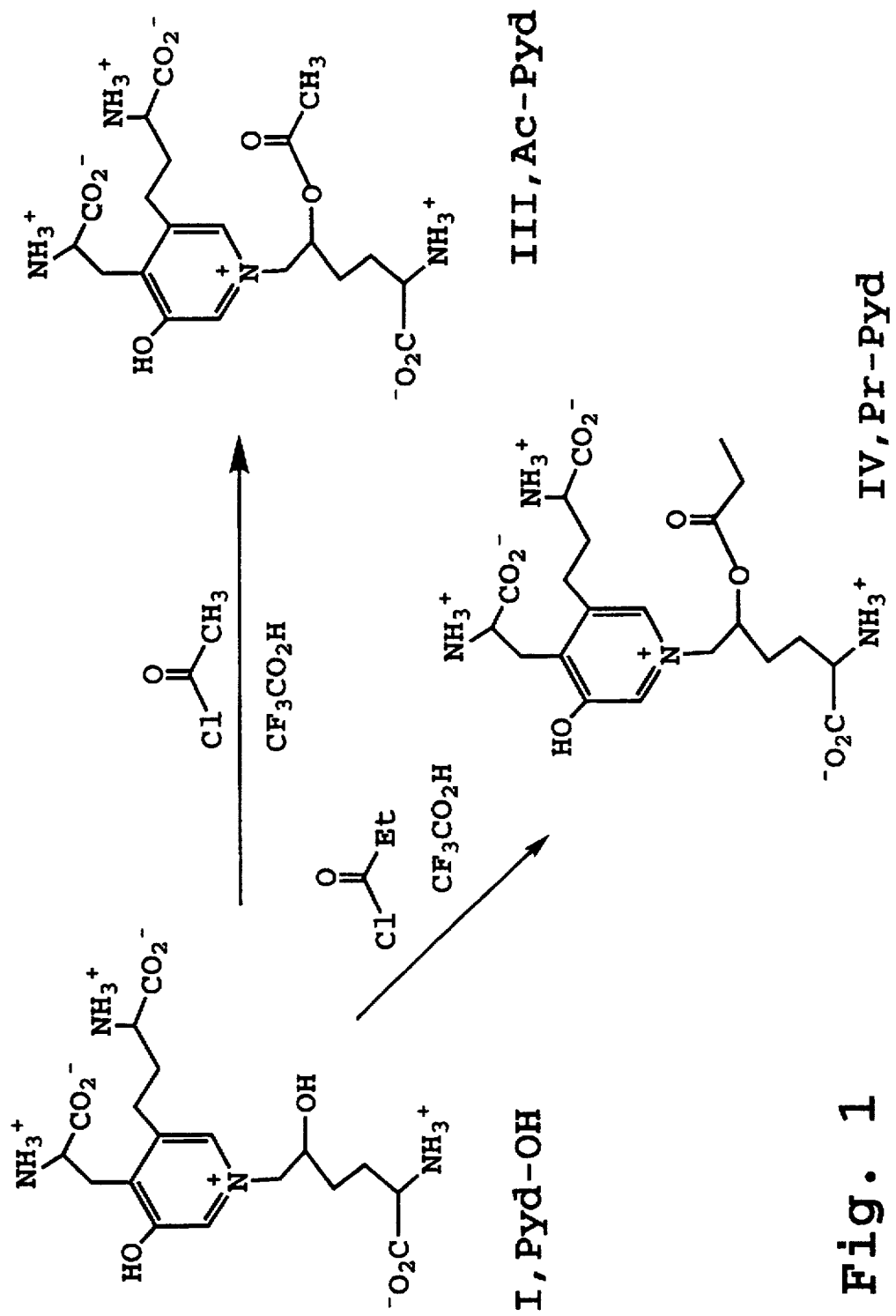
FIG. 1 shows reaction schemes for acylating the aliphatic hydroxyl group of pyridinoline using acetyl chloride and propionyl chloride.

FIG. 1 shows reaction schemes for preparing exemplary O-acylated pyridinoline derivatives of the present invention. In general, such derivatives are prepared by adding a thoroughly dried sample of pyridinoline (Pyd) to a mixture containing anhydrous trifluoroacetic acid (TFA) and an acylating agent (e.g., acetyl or propionyl chloride). Typically, the ratio of TFA to the acylating agent is about 9:1 (v:v). The reaction vial is then sealed and allowed to react for a time sufficient to selectively acylate the aliphatic hydroxyl group of Pyd. Suitable reaction times vary, but are typically 20–60 minutes in duration (see Examples 1 and 2). The reaction is then stopped by the addition of water, and the solvent is removed by evaporation.

Figure 2:
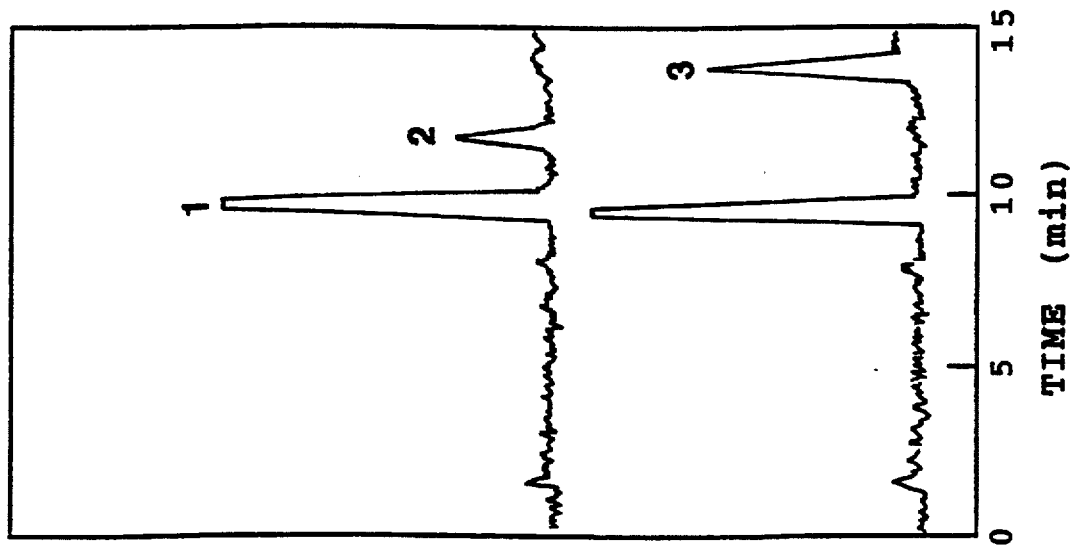
FIG. 2 shows relative elution times in reversed phase C18 HPLC of Ac-Pyd (peak 2) and Pr-Pyd (peak 3) relative to pyridinoline (peak 1).

The extent of conversion of Pyd to the corresponding O-acylated derivative can be assessed by reversed phase C18 HPLC. Specifically, as illustrated in FIG. 2 and detailed in Example 1, acylation of Pyd with acetyl chloride or propionyl chloride produces acylated derivatives having retention times close to but distinct from that of Pyd. Thus, the time course of the reaction can be monitored by following the loss of Pyd and the appearance of the acylated derivatives. In addition, preparative amounts (e.g., milligram quantities) of acylated Pyd can be obtained having greater than 97% purity, as described in Example 2.

The acylation method is characterized by an extent of acylation of Pyd starting material of greater than 80% completion. However, to obtain such a high extent of acylation, anhydrous reaction conditions must be employed. Use of non-anhydrous TFA or of incompletely dried Pyd can diminish or even preclude attainment of the desired product. In addition, the reaction should not be allowed to proceed for too long a time (~several hours) in order to avoid degradation of the acylated product, and thus, a decreased yield. Thus, an optimal reaction time should be determined for a particular set of reaction conditions by monitoring by HPLC analysis a trial reaction mixture for several hours. Carboxylic acid bromides can be used in place of the acid chlorides, generally leading to faster acylation rates than observed for the corresponding acid chlorides.

The acylation procedure of the present invention can be used to produce a variety of pyridinoline derivatives selectively acylated at the aliphatic hydroxyl group of Pyd. Acylating reagents having various linear, branched chain, or cyclic alkyl groups (e.g., n-butanoyl chloride and isopropanoyl chloride, or cyclohexanecarbonyl chloride) as well as reagents having aromatic groups (e.g., benzoyl chloride) can be used to produce Pyd derivatives having different chromatographic retention times than Pyd. In addition, as described in a later section, Pyd can be derivatized with other chemical groups to anchor Pyd to a carrier protein for use as an immunogen, or to anchor Pyd to a solid support.

Evidence that the acylation conditions described above afford selective acylation of the aliphatic hydroxyl group of Pyd (and not the ring hydroxyl, for example) was obtained by UV-visible and $^1$H-NMR spectroscopies.

It has been shown that aqueous Pyd undergoes a bathochromic shift when the pH is changed from acidic (pH~1) to neutral or alkaline (pH 7.4 or ~13) (Fujimoto et al., 1977). This shift is attributed to conversion of the Pyd ring-hydroxyl group (pKa~4.2) from the protonated form ($\lambda$max ~295 nm) to the unprotonated form ($\lambda$max~325 nm), a shift that cannot occur if the ring hydroxyl group has been acylated.

Accordingly, to determine whether the ring-hydroxyl group had been acetylated in the acylation procedure of the present invention, UV-visible spectra of acetylated Pyd were recorded under acidic and neutral pH conditions (Example 3). As detailed in Example 3, the UV-visible absorbance behavior of acetylated Pyd closely resembles that of Pyd itself. Under acidic conditions (pH~3), the spectrum of acetylated Pyd showed an absorbance peak at 294 nm. Moreover, when the pH was adjusted to about 7, the peak shifted to 326 nm. These results show that the ring-hydroxyl oxygen in acetylated Pyd is not acetylated.

Figure 3A:
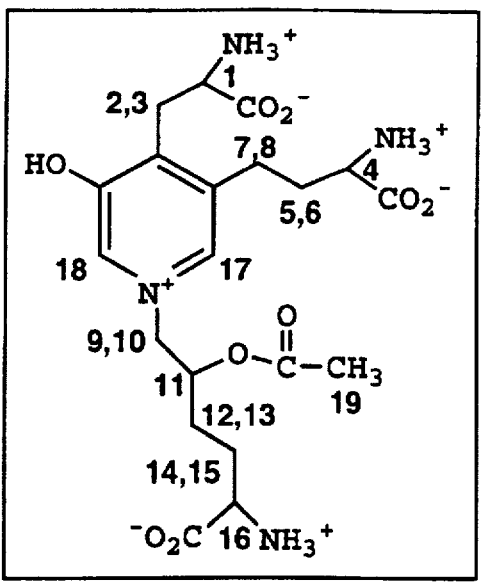
FIGS. 3A–3B show a numbering scheme 3A) and a high field $^1$H nuclear magnetic resonance spectrum (3B) of Ac-Pyd in deuterium oxide solvent.
Figure 3B:
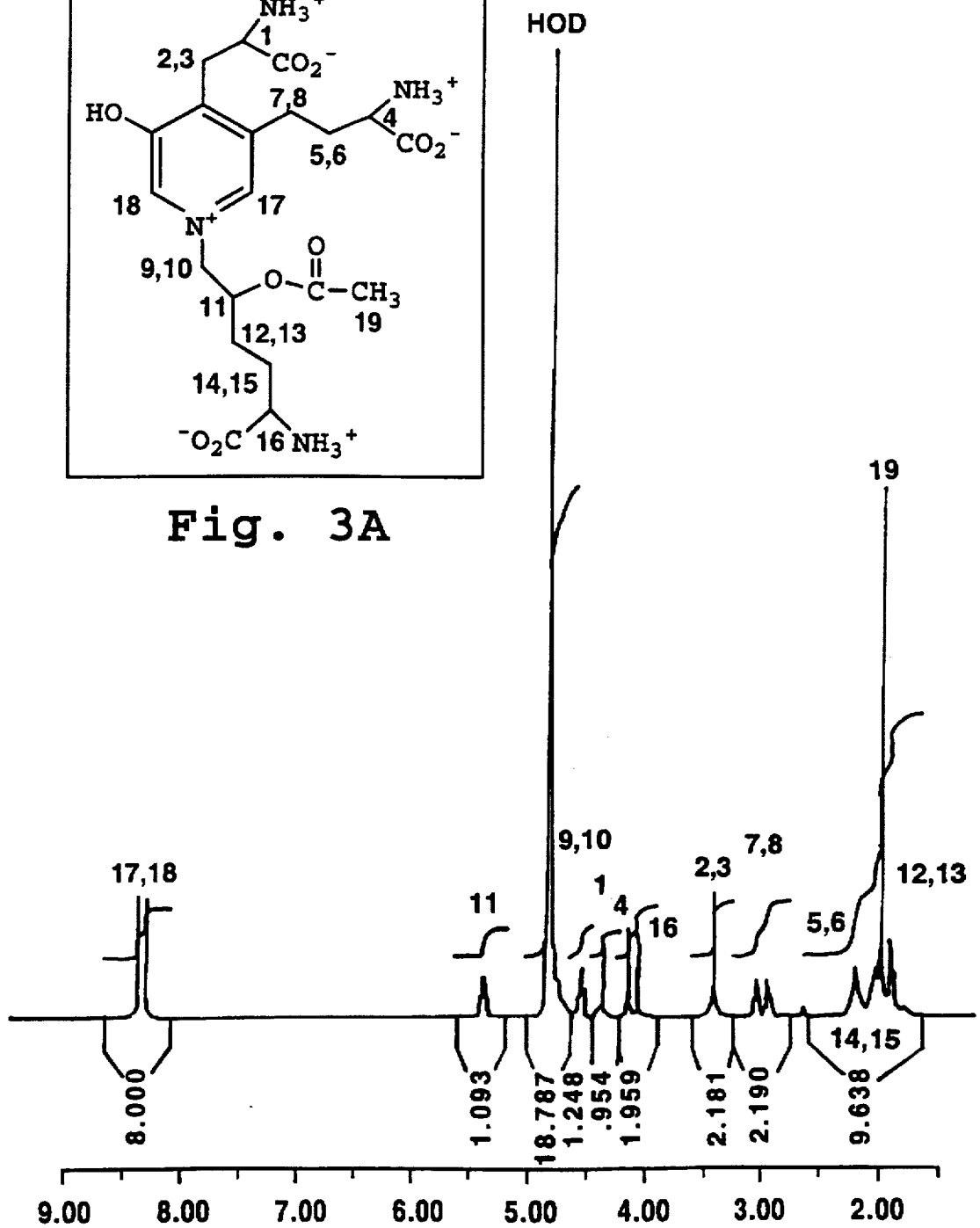

To obtain further evidence that only the aliphatic hydroxyl group of Pyd had been acylated, acetylated Pyd prepared as in Example 2 was characterized by high-field $^1$H NMR spectroscopy (FIGS. 3A and 3B).

TABLE 1

| Pyd[a] δ-Shift | Ac-Pyd[a] δ-Shift | peak properties[a] (mult., integral, assignment) |
|---|---|---|
| 8.10 | 8.35 | (s, 1, ring-2 or 6: ArH) |
| 8.05 | 8.28 | (s, 1, ring-2 or 6: ArH) |
| ~4.5 | ~4.8 | (dd, 1, ring-N: NCH$_2$)[b] |
| 4.17 | 4.54 | (dd, 1, ring-N: NCH$_2$)[c] |
| 3.99 | 4.36 | (t, 1, ring-4: RCH(NH$_3^+$, CO$_2^-$) |
| 3.92 | 5.36 | (m, 1, R$_2$CHOH/R$_2$CHOAc) |
| 3.79 | 4.14 | (t, 1, ring-5: RCH(NH$_3^+$, CO$_2^-$) |
| 3.76 | 4.04 | (t, 1, ring-N: RCH(NH$_3^+$, CO$_2^-$) |
| 3.22 | 3.40 | (d, 2, ring-4: CH$_2$)* |
| 2.84 | 3.04 | (m, 1, ring-5: Ar—CH$_2$) |
| 2.73 | 2.93 | (m, 1, ring-5: Ar—CH$_2$) |
| 2.04 | 2.19 | (m, 2, ring-5: CH$_2$CH(NH$_3^+$, CO$_2^-$)* |
| 1.96 | 2.19 | (m, 1, ring-N: CH$_2$CH(NH$_3^+$, CO$_2^-$)* |
| 1.84 | 2.03 | (m, 1, ring-N: CH$_2$CH(NH$_3^+$, CO$_2^-$)* |
| 1.58 | 1.98 | (m, 1, ring-N: γ-CH$_2$) |
| 1.47 | 1.88 | (m, 1, ring-N: γ-CH$_2$) |
| — | 1.96 | (s, 3 expected, CH$_3$C(=O)O)* |

[a]See structure I at FIG. 1. The peack multiplicities and integrations for Ac-Pyd were essentially the same as for Pyd.
[b]Ring-N: NCH$_2$ proton, obscured by HOD peak.
[c]Ring-N: NCH$_2$ proton, not obscured by HOD peak.
*The indicated integration values for these peaks were measured individually only with Pyd. Individual integration of these peaks was not possible for Ac-Pyd due to peak overlaps; however, for Ac-Pyd, integration of the asterisk-marked peaks together summed to 9.6. The sharp singlet at 1.96 ppm was observed only for Ac-Pyd.

With reference to Table 1, it can be seen that the shift values for many of the proton groups had not changed significantly after acetylation of Pyd. Notably, however, Ac-Pyd exhibited a new singlet at 1.96 ppm, consistent with the presence of an acetyl methyl group. Although this peak could not be integrated separately, integration of the singlet and surrounding peaks (~2.25 to ~1.8 ppm) showed a value of 9.6, very close to the value of 9.0 expected for an acetyl methyl group (3 hydrogens) plus three methylenes (6 hydrogens). In addition, the peak at 3.92 ppm for the methine hydrogen vicinal to the aliphatic hydroxyl group of Pyd was absent from the spectrum of Ac-Pyd, and instead, a new peak at 5.36 ppm had appeared. This large change in δ-shift is expected for conversion of the aliphatic hydroxyl group to an acetyl group (Roberts and Casserio, 1977). These results, together with those obtained above by UV-visible spectroscopy, show that Pyd is selectively acylated at its aliphatic hydroxyl group under the acylation conditions of the present invention.

III. Use of an O-Acylated-Pyridinoline as an Internal Standard for Crosslinks on HPLC In one aspect of the invention, an acylated pyridinoline derivative, as exemplified by O-acetylpyridinoline, is employed as an internal standard for quantitating pyridinoline crosslinks fractionated by HPLC.

This use of the acetylated derivative is illustrated by an assay method for quantitating native or hydrolysed Pyd in a urine or serum sample, as a diagnostic tool for detecting bone collagen disorders. In the assay method, a body-fluid sample, preferably a urine sample, is combined with a known amount of the acetylated derivative. The sample material is then pretreated, e.g., by contacting the sample components with cellulose or nitrocellulose, to remove some of the non-crosslink components in the sample, particularly peptide components. However, some Pyd may be lost during pretreatment by non-specific binding of Pyd to the solid phase pretreatment material (e.g., cellulose powder). Studies conducted in support of the present invention have shown that the amount of Pyd removed by the pretreatment step is variable, but does correlate closely with the amount of derivatized Pyd which is removed in pretreatment (see Example 7). Thus, the derivatized Pyd serves in part as an internal standard to correct for losses of Pyd which can occur on pretreatment.

The pretreated material is then analyzed by fractionation by HPLC, as exemplified by reversed phase C18 HPLC, to separate the crosslink components in the sample. Examples 5 to 9 below describe several HPLC fractionations of hydrolysed and non-hydrolysed urine samples, after addition of derivatized-Pyd internal standard and pretreatment by cellulose chromatography.

Figures 5A, 5B, 5C:
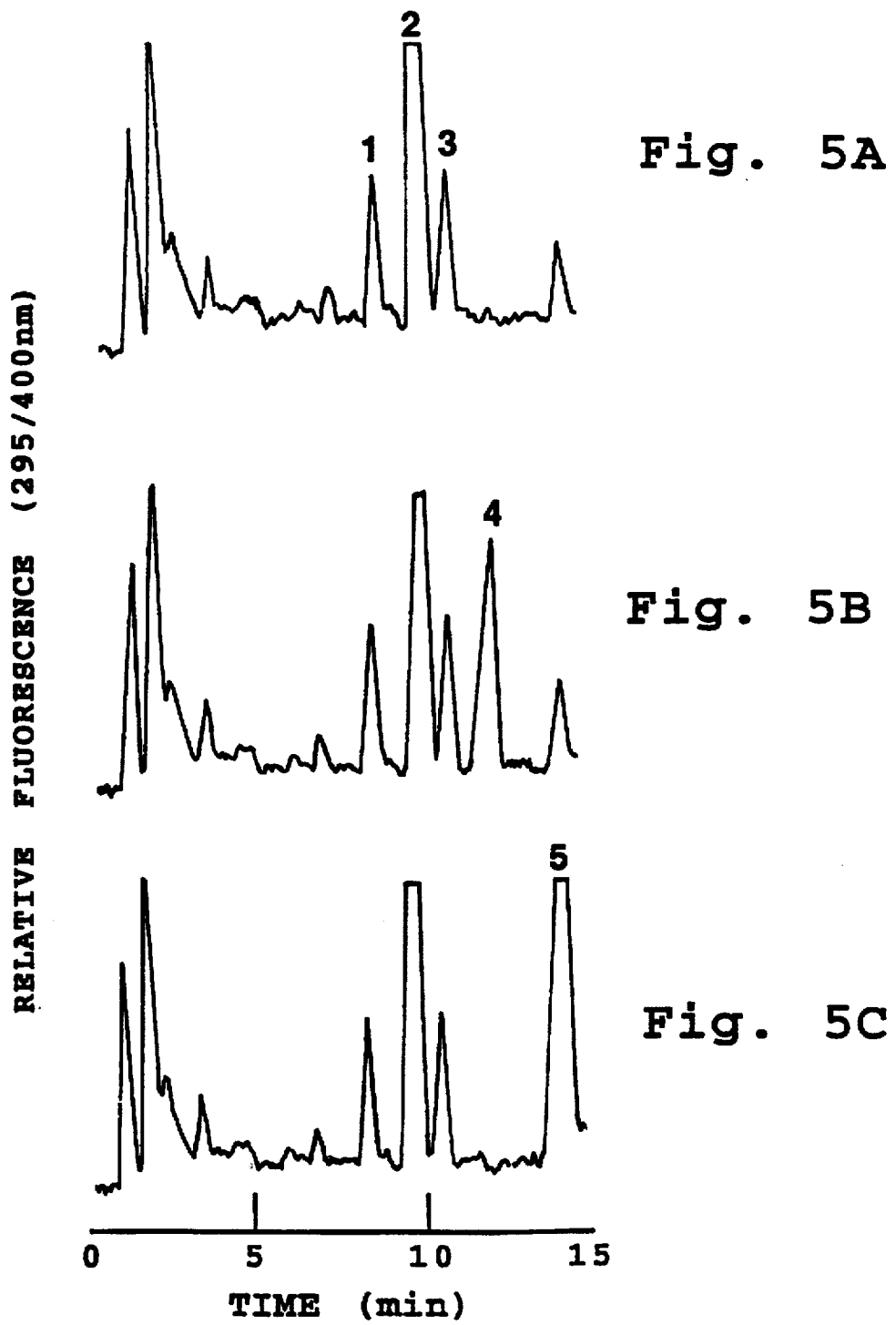
FIGS. 5A–5C show reversed phase C18 HPLC chromatograms of a fractionated, unhydrolyzed human urine sample (5A), the urine sample with added Ac-Pyd (5B), and the urine sample with added Pr-Pyd (5C). Peak identification: 1, glycosylated Pyd; 2, Pyd; 3, Dpd; 4, Ac-Pyd; 5, Pr-Pyd.

In the method described in Example 4, Ac-Pyd or Pr-Pyd was added to a pre-extracted, unhydrolyzed urine sample and then analyzed by C18 HPLC. As seen in FIGS. 5A–5C (see Example 4 for details) Ac-Pyd (peak 4, FIG. 5B) migrated with a retention time distinct from both the retention times of Pyd and Dpd (peaks 2 and 3, respectively), and also from the retention times of the other fluorescent components of the urine sample. Pr-Pyd (peak 5, FIG. 5C) migrated uniquely with respect to Pyd and Ac-Pyd, but comigrated with a urine component.

Figure 6A:
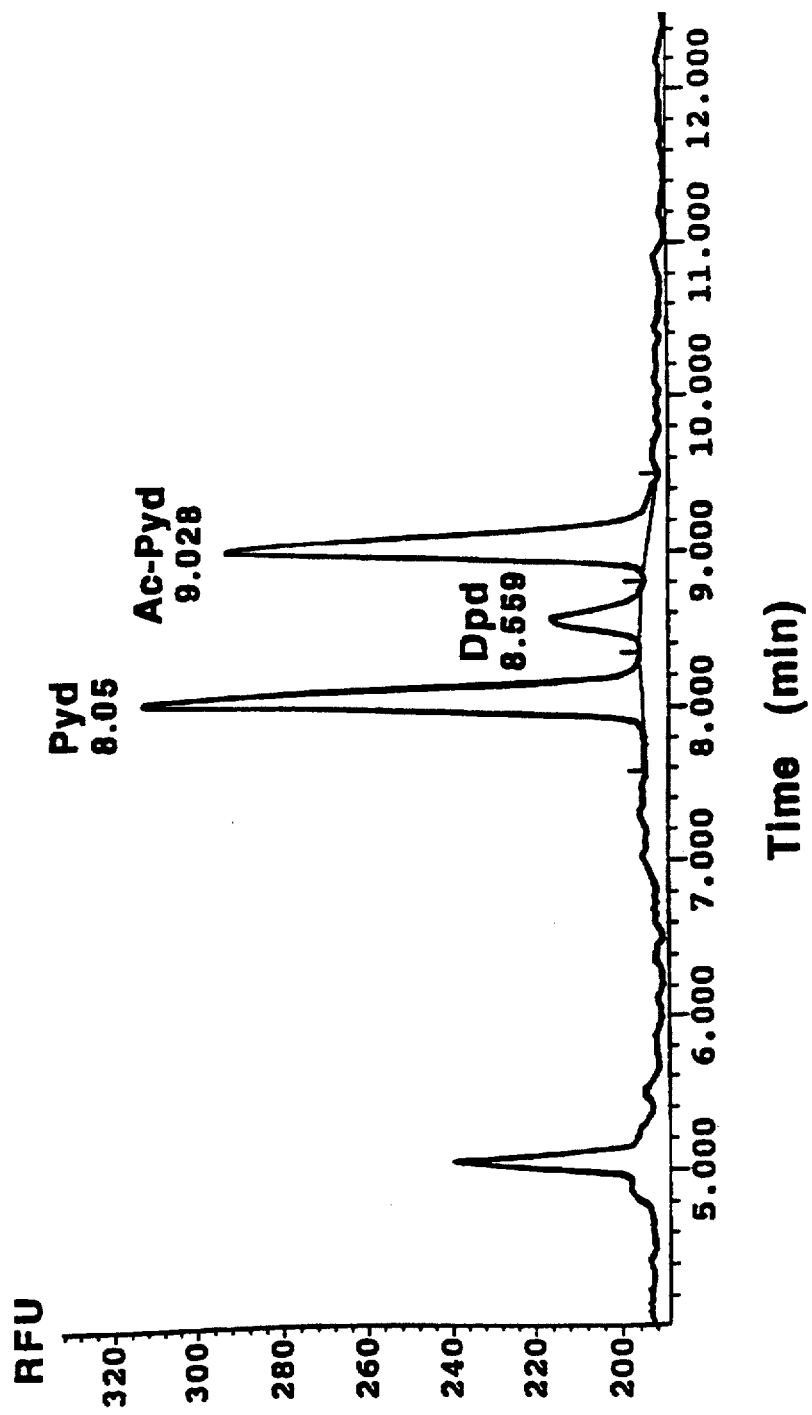
FIGS. 6A–6C show reversed phase C18 HPLC chromatograms of crosslinks extracted from hydrolyzed urine samples by cellulose chromatography.

An exemplary method for extracting and analyzing crosslinks in a urine sample is described in Example 5. In the method, the urine sample is mixed with 1 volume of 90% acetic acid containing 200 nM Ac-Pyd, and 4 volumes of butanol. The mixture is loaded onto a cellusose column, and the column is washed with mobile phase (4:1:1 butanol:acetic acid:water) to elute non-crosslink components. The residual butanol is removed by washing the column with dimethylformamide (DMF). FIG. 6A shows a representative HPLC chromatogram of a hydrolysed urine sample containing Ac-Pyd added as an internal standard, obtained according to the procedure just outlined. Both Pyd and Dpd in the sample are cleanly resolved from one another and from Ac-Pyd. In quantitating either Pyd or Dpd, the peak areas of the three peaks can be integrated, and the relationship between peak area and total Pyd can be determined from the Ac-Pyd peak. Details are given in Example 5.

Figure 6B:
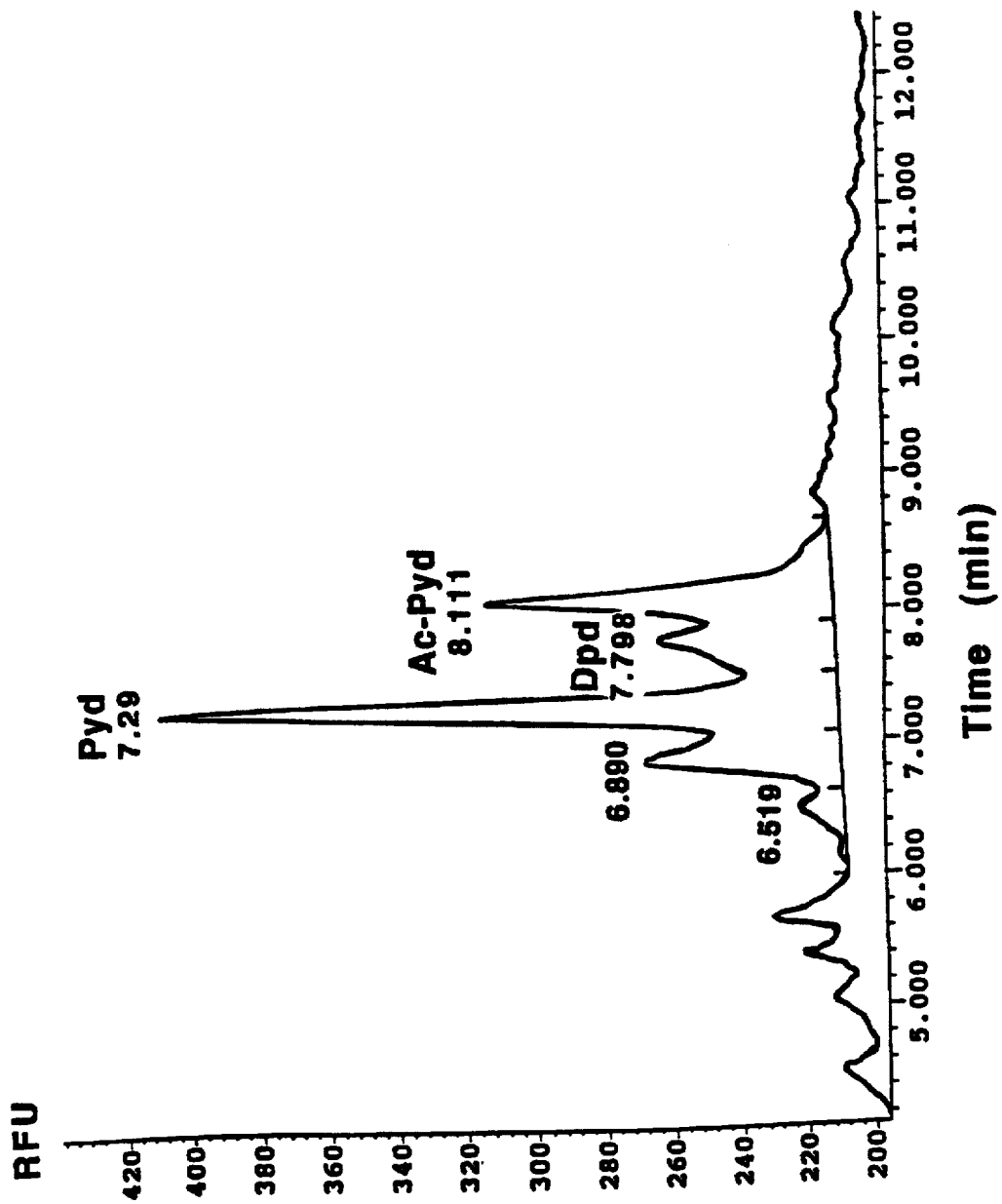
Figure 6C:
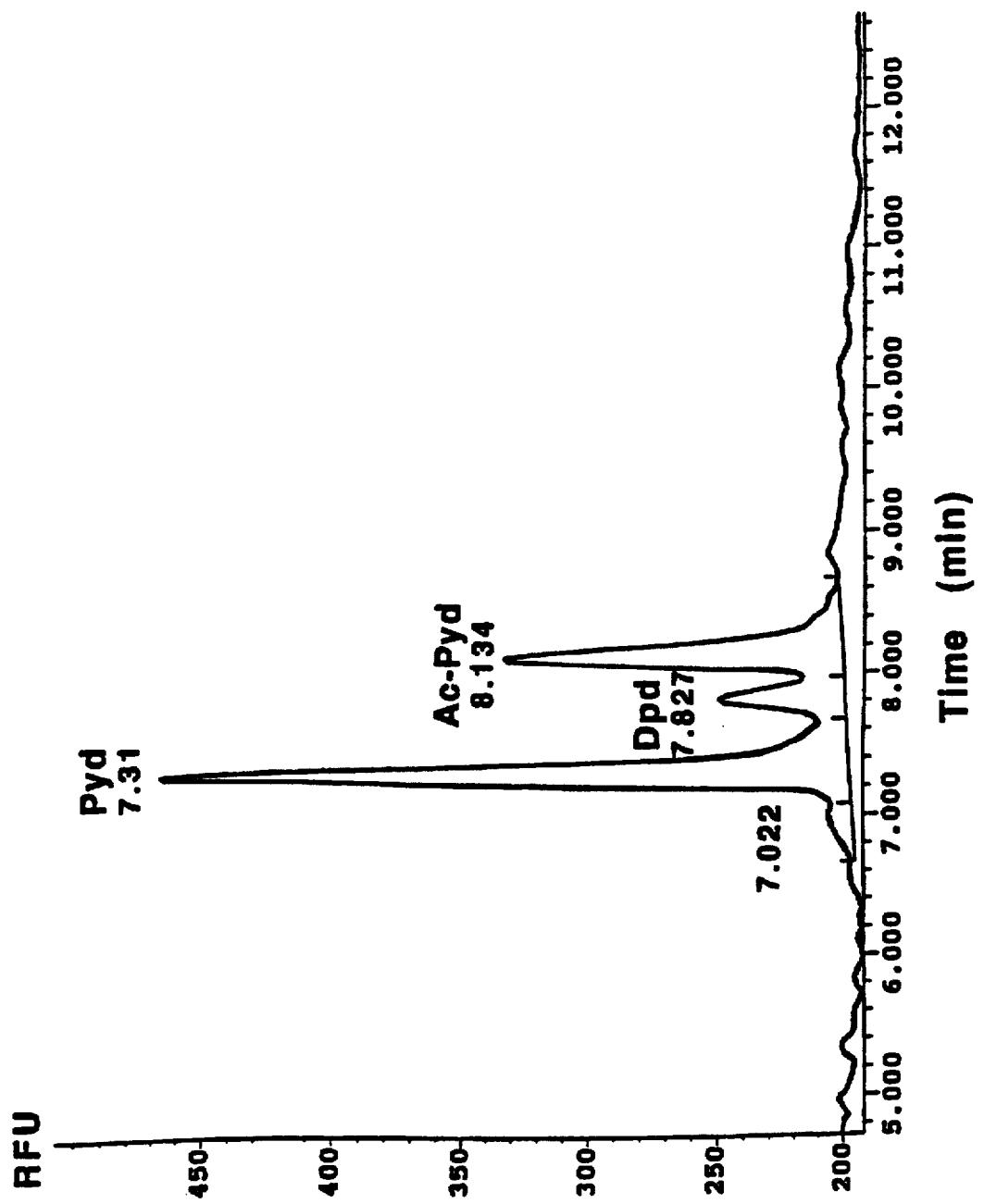

FIGS. 6B and 6C are HPLC chromatograms of hydrolysed urine samples containing high levels of creatinine (about 25 mM). In the FIG. 6B chromatogram, the procedure discussed above with respect to FIG. 6A was used, except the residual butanol is removed by washing the column with tetrahydrofuran (THF). The FIG. 6C chromatogram was obtained as above, by removing residual butanol with DMF. As seen, the cleaner separation is achieved, at high creatinine sample levels, when the residual butanol in the column is removed by DMF washing. Details are given in Example 6.

The accuracy and reliability of the method, for quantitating Pyd by HPLC is demonstrated by the study in Example 7. Here a series of urine samples containing known amounts of Pyd and a known fixed amount of Ac-Pyd were fractionated by HPLC, as above, including cellulose pretreatment, and the amount of Pyd recovered was determined from the peak area for Pyd in the chromatogram, corrected for the peak area of the Ac-Pyd calibrant. The corrected Pyd values are plotted against the expected Pyd values (the amount of Pyd originally present in the sample prior to cellulose pretreatment) in FIG. 7. A least squares analysis gives a slope of 1 with an R value of 0.997.

Figure 8:
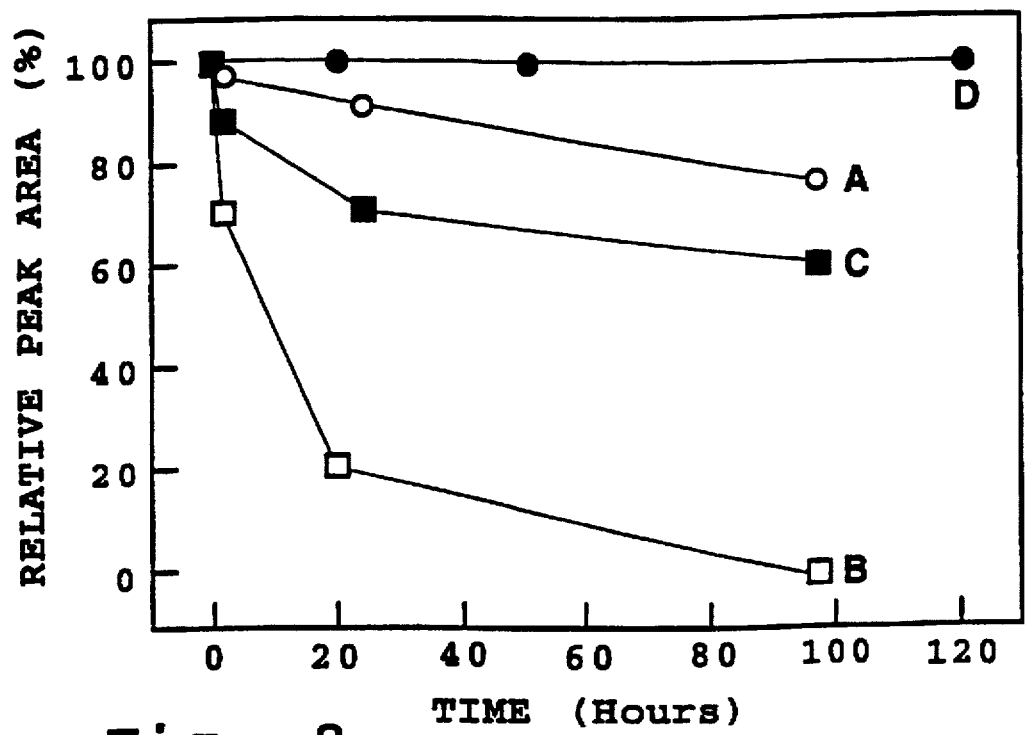
FIG. 8 illustrates the stability of Ac-Pyd in various mixtures of acetic acid, water, and added acetic anhydride. A: acetic acid; B: acetic acid containing 0.1% acetic anhydride; C: 90% acetic acid in water, additionally containing 0.1% acetic anhydride; and D: 90% acetic acid in water (no acetic anhydride added).

FIG. 8 shows the stability of the Ac-Pyd compound under different solvent conditions. In each of the four plots, Ac-Pyd was held in an HPLC reservoir in the four solvents described in Example 8. At various times up to 5 days, aliquots were analyzed by HPLC and the amount of Pyd quantitated by peak area. As seen from FIG. 8, the Ac-Pyd was substantially unchanged over a five day period in 90% acetic acid/10% water, but was degraded to various degrees in the other solvents (which contained acetic anhydride). The results show the importance of avoiding acetic anhydride in the storage solution.

It can be appreciated from the foregoing that the derivatized Pyd provides a number of advantages as an internal standard for Pyd, in the above Pyd assay using HPLC. First, the derivative is recoverable in substantially the same yield as Pyd and Dpd after pretreatment steps and in HPLC chromatographic separation. Secondly, the derivative is characterized by a retention time close to, but distinct from, the retention times of urinary Pyd and Dpd crosslinks in chromatographic analysis (e.g., reversed phase C-18 HPLC). Finally, the derivative has spectroscopic (e.g. UV-visible absorbance and fluorescence) properties similar to Pyd.

IV.A. Preparation of a Pyridinoline Immunogen

For use in obtaining antibodies selective for Pyd, a pyridinoline immunogen (hapten) can be prepared by conjugation of a carrier molecule, typically a carrier protein such as keyhole limpet hemocyanin or bovine serum albumin, to the aliphatic hydroxyl group of Pyd. The Pyd may be native or hydrolyzed Pyd, for selectively generating antibodies that bind native and hydrolyzed Pyd, respectively.

Exemplary methods for coupling the aliphatic hydroxyl group of Pyd to a carrier protein are outlined in FIGS. 9A–9B and 10A–10F. In one general approach, the carrier protein and the aliphatic hydroxyl group of Pyd are derivatized such that the resultant derivatives can be coupled via reaction of a sulfhydryl group with a maleimide group or an activated sulfhydryl group. In another general approach, the aliphatic hydroxyl group of Pyd is converted to a sulfhydryl group which can then be coupled to a carrier protein as above. An excellent compilation of coupling reagents and methods can be found in Wong (1991), which is incorporated herein by reference as representative of background art.

Figure 9A:
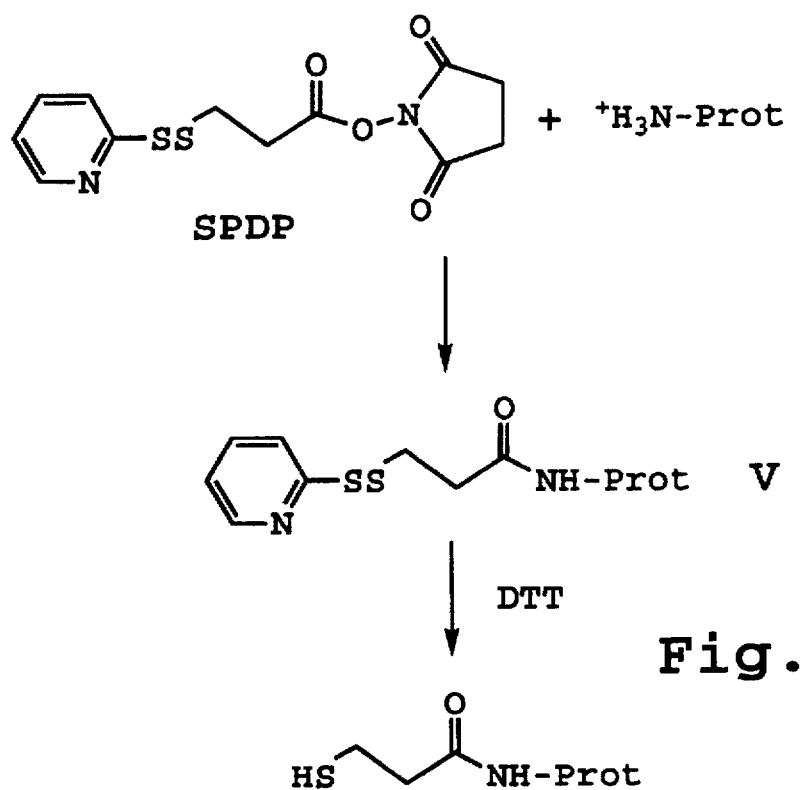
FIGS. 9A and 9B illustrate reaction schemes for preparing derivatized carrier proteins.
Figure 9B:
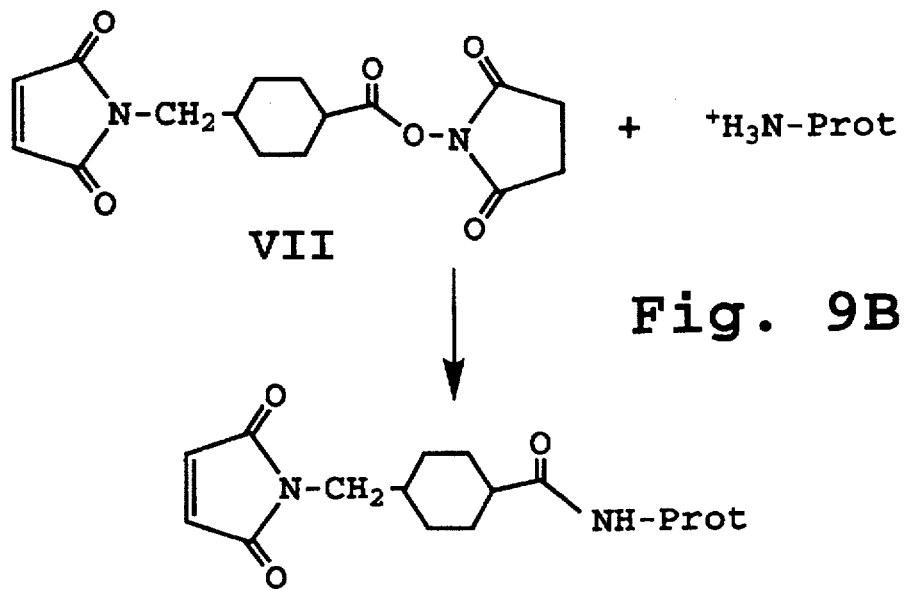

FIGS. 9A and 9B illustrate well known methods by which the amino groups of a carrier protein can be derivatized to contain sulfhydryl groups or maleimide groups (Wong, 1991, and references therein). In FIG. 9A, the carrier is reacted with succinimidyl 3-(2-pyridyldithio)propionate (SPDP) to produce acylated adduct V. Treatment of V with dithiothreitol (DTT) yields a thiolated (i.e., sulfhydryl-containing) protein VI, "Prot-SH". In FIG. 9B, the carrier is reacted with N-succinimidyl 4-(N-maleimidomethyl) cyclohexane-1-carboxylate VII (SMCC) to produce a carrier VIII that contains maleimide groups.

Figure 10A:
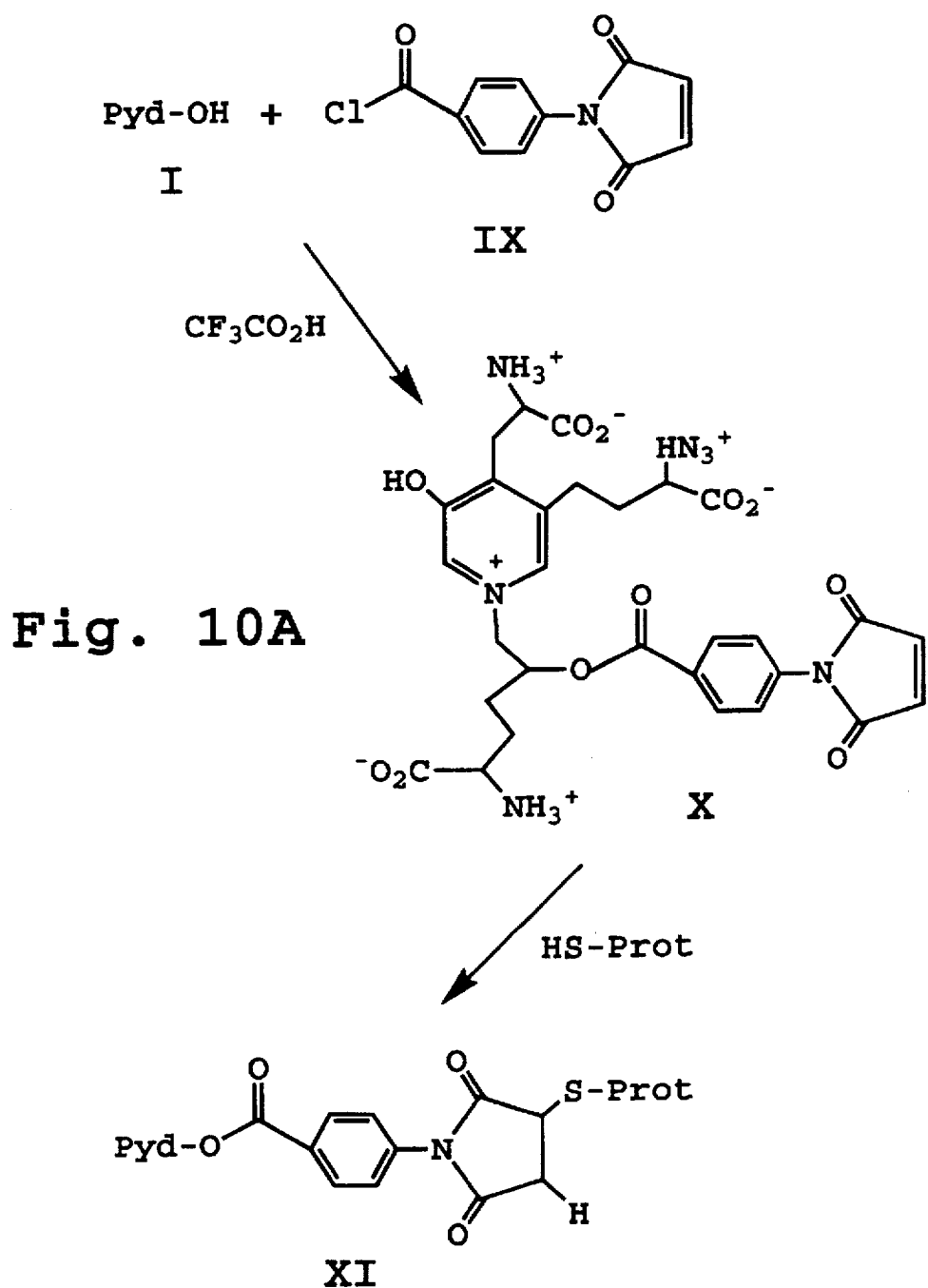
FIGS. 10A–10F illustrate reaction schemes for preparing pyridinoline-carrier protein conjugates.

FIGS. 10A-10D illustrate methods by which the aliphatic hydroxyl group of Pyd can be derivatized and then coupled to the derivatized carriers of FIGS. 9A and 9B. In FIG. 10A, Pyd is acylated with 4-chloroacetylphenylmaleimide (IX) in anhydrous TFA to give maleimide-containing derivative X. Derivative X is then reacted with a thiolated carrier (Prot-SH) to produce immunogen XI.

Figure 10B:
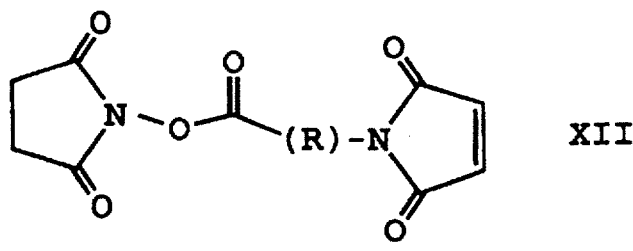
Figure 10B:
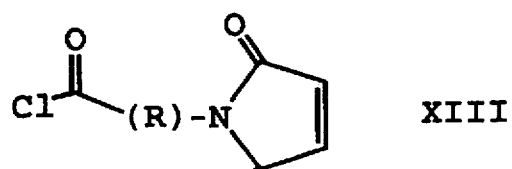
Figure 10B:

FIG. 10B shows how other maleimide-containing acylating agents, e.g., N-succinimidyl maleimidoacetate (Sigma Chemical Co.), N-succinimidyl 3-maleimidopropionate (Aldrich Chemical Company or Sigma), N-succinimidyl 4-p-maleimidophenyl)butyrate (Pierce Chemical Co.) and the like, can be prepared from commercially available compounds. In general, the N-hydroxylsuccinimide group of XII is removed by hydrolysis, and the resultant carboxylic acid is converted to an acid chloride XIII using thionyl chloride. The acid chloride is then used to produce a Pyd-containing immunogen as in FIG. 10A.

Figure 10C:
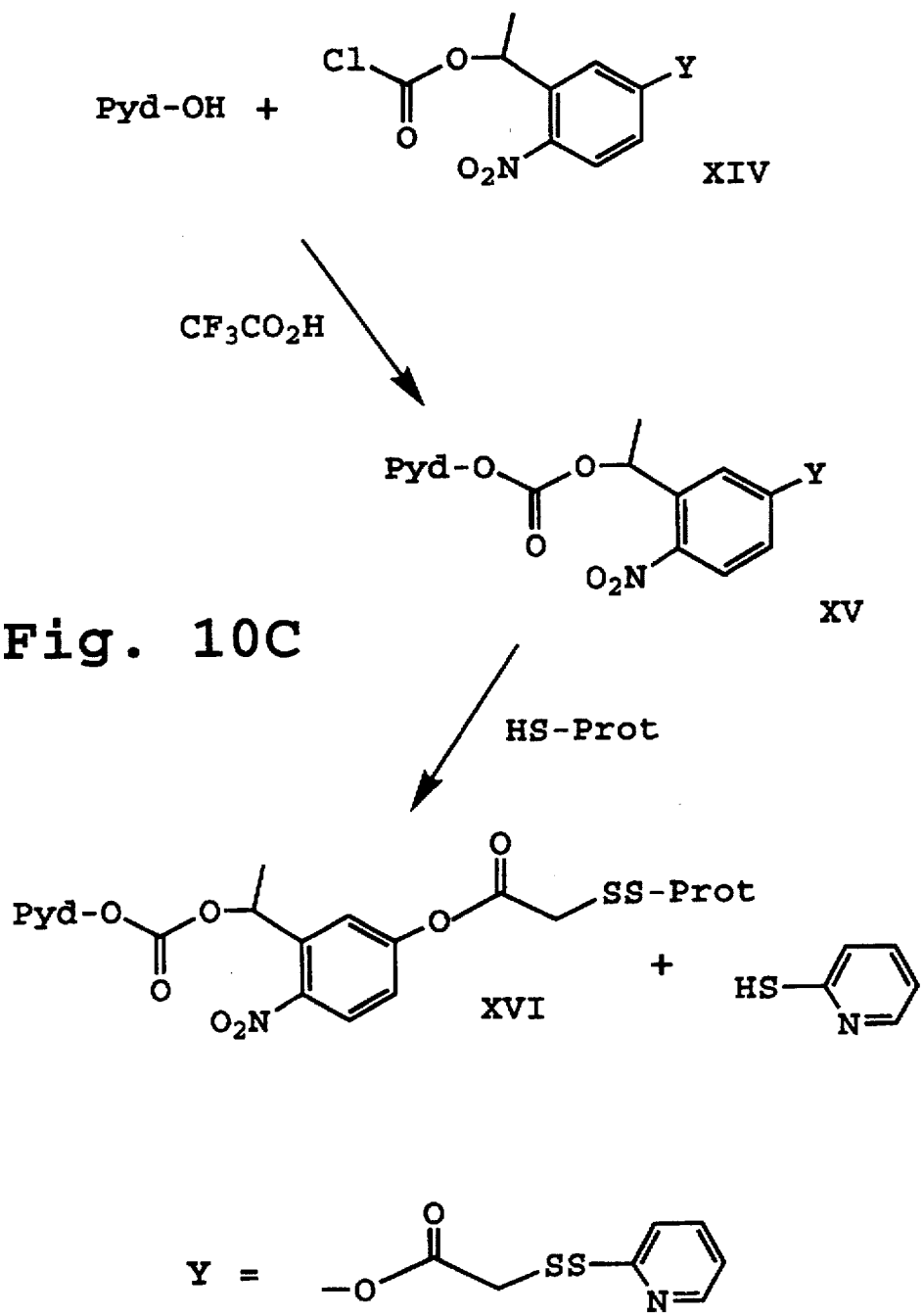

FIG. 10C shows a reaction scheme in which the aliphatic hydroxyl of Pyd is derivatized with an acylating agent XIV, [4-nitro-3-(1-chlorocarbonyloxyethyl)phenyl]methyl-3-(2-pyridyldithiopropionic acid) ester, that contains a masked sulfhydryl that is activated towards thiol exchange. The resultant carbonate XV is then reacted with HS-Prot, (e.g. VI from FIG. 9A) to produce an immunogen having a disulfide linkage.

Figure 10D:
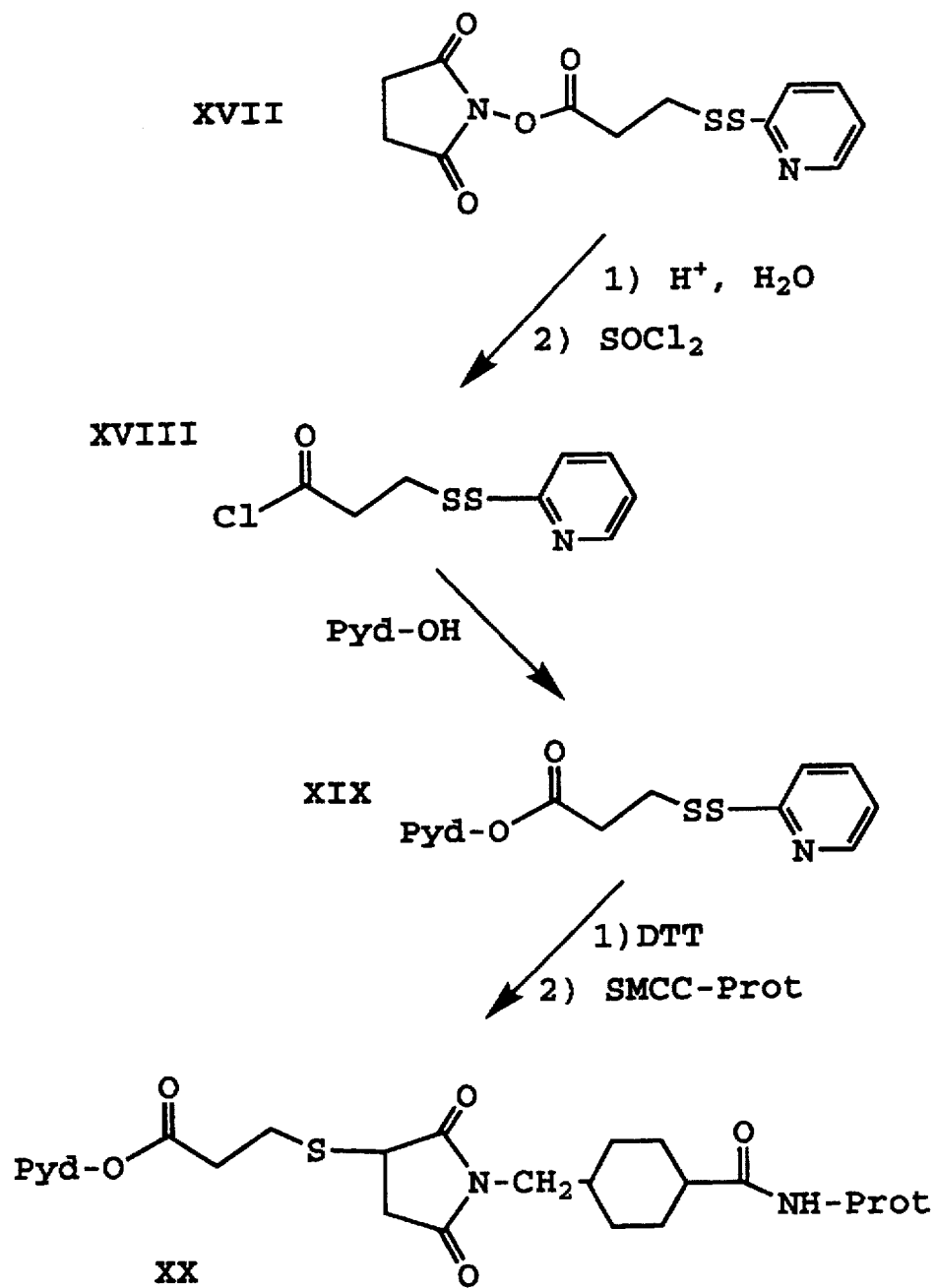
Figure 10E:
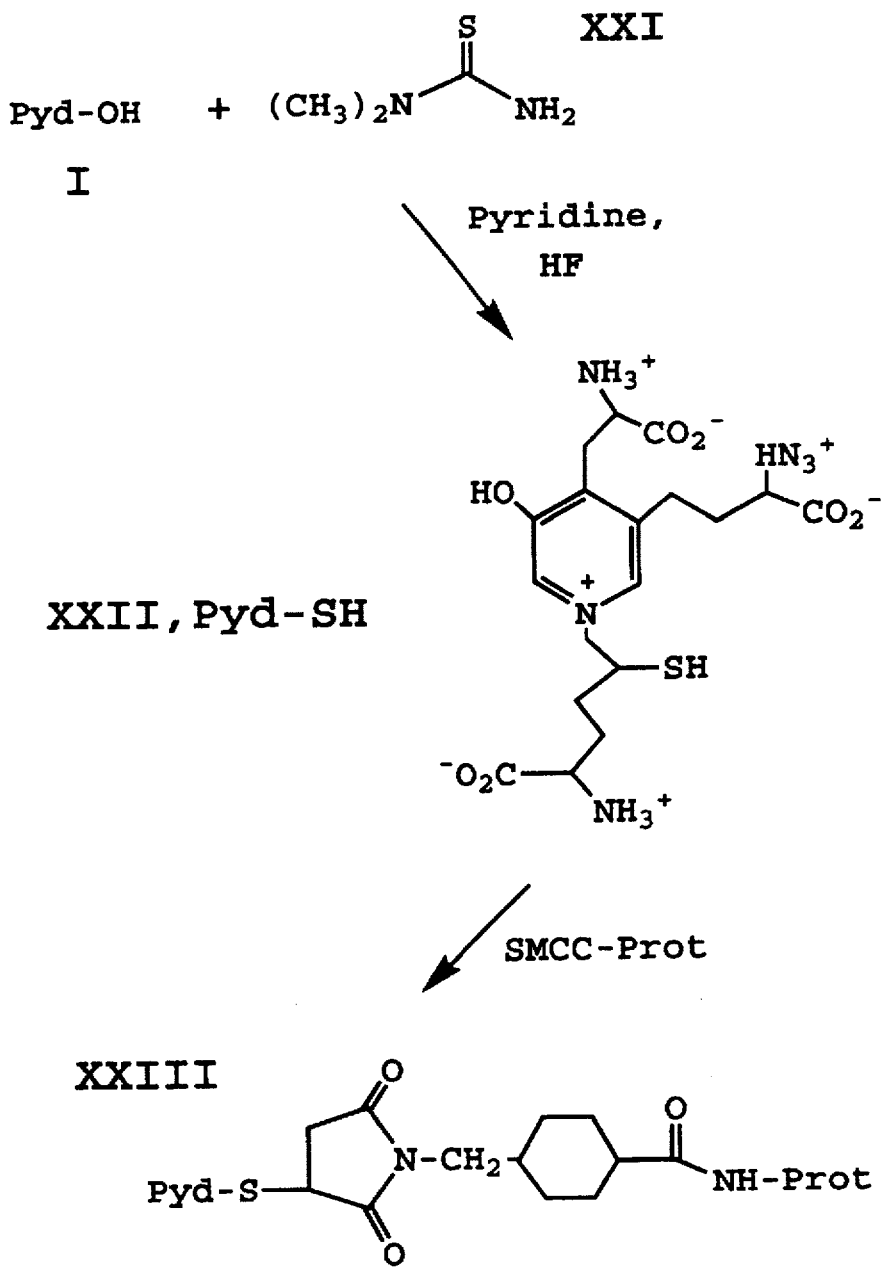

Derivatization of Pyd with another masked-sulfhydryl-containing agent is shown in FIG. 10D. Following preparation of acid chloride XVIII from N-succinimidyl 3-(2-pyridyldithio) propionate XVII, the acid chloride is reacted with Pyd to produce acylated Pyd XIX. The 2-thiopyridine group is then removed using dithiothreitol (DTT), and the resultant Pyd derivative is reacted with a maleimide-containing carrier (SMCC-Prot) to produce immunogen XX. FIGS. 10C and 10E thus illustrate two was in which an acylated Pyd containing a masked thiol (e.g., structures XV and XIX) can be coupled to a carrier protein.

Figure 10F:
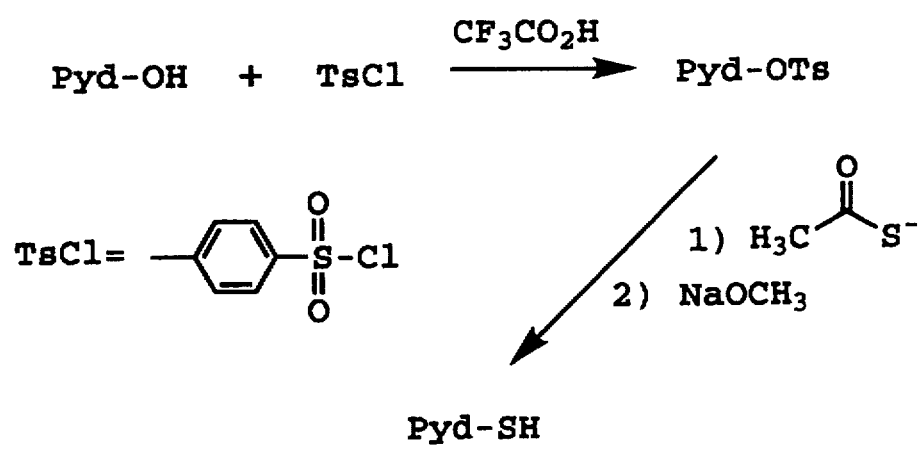

FIGS. 10E and 10F illustrate schemes in which the aliphatic hydroxyl group of Pyd is converted to a sulfhydryl group. In FIG. 10E, Pyd is treated with N,N-dimethylthiourea XXI in HF/pyridine, thereby producing Pyd-SH XXII, a sulfhydryl analog of Pyd. This analog can then be coupled to a maleimide-containing carrier (SMCC-Prot) to produce immunogen XXIII.

In FIG. 10F, the aliphatic hydroxyl is tosylated using tosyl chloride in TFA. The resultant tosylated Pyd is then reacted with thioacetate to produce a thioacetyl-Pyd which is then treated with aqueous sodium methoxide to remove the acetyl group, thereby producing Pyd-SH for coupling to a carrier as in FIG. 10E.

The Pyd-protein conjugates prepared by above methods can be used to prepare monoclonal or polyclonal antibodies by conventional methods (e.g., Harlow, 1988).

VI.B. Preparation of Pyd-Coated Solid-Phase Reagent

Figure 11:
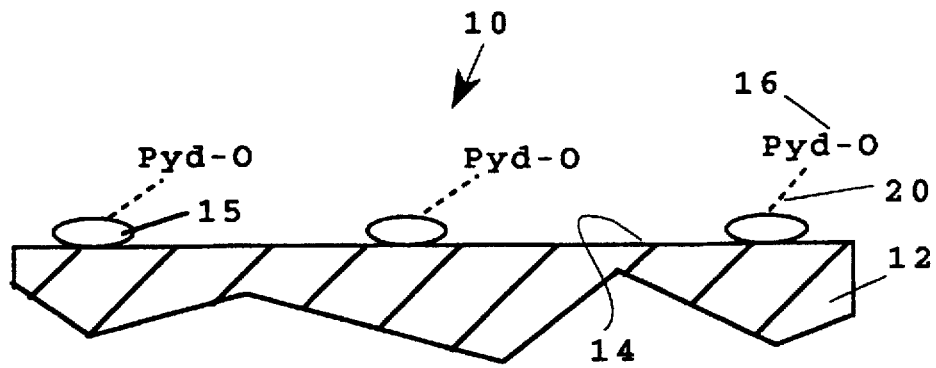
FIGS. 11 illustrates a solid support surface of the present invention.

The Pyd derivatization method forming part of the invention can also be applied to forming a Pyd-coated solid-phase reagent. The reagent may be used, for example, as an affinity chromatography reagent, for purification of anti-Pyd antibodies, or in another example, may be used in a solid-phase immunoassay device. The latter application is illustrated in FIG. 11, which shows a solid-phase reagent 10 which includes a solid-phase support 12 having surface attached binding Pyd molecules effective to bind anti-Pyd antibodies. A variety of glass and polymer resin supports having chemically derivatizable groups, or surfaces effective in protein adsorption may be used as the solid support. In one preferred embodiment, the solid support is coated with protein, e.g., adsorbed human serum albumin which is derivatized with streptavidin, indicated at 15 in the figure. Pyd is derivatized with biotin, according to the derivatization methods described above. Briefly, biotin is derivatized to provide maleimide or sulfhydryl groups, and the modified biotin is reacted with a thiolate or maleimide group containing derivative, prepared as above. The biotin-Pyd conjugate is then attached to the solid support through high-affinity streptavidin-biotin binding, indicated by dashed lines in the figure.

Alternatively, Pyd can be derivatized directly to the support by first derivatizing a solid support, such as support 12, to contain maleimide or sulfhydryl groups. The support is reacted with Pyd functionalized with a thiolate or maleimide group, according to the method of the invention, to couple the Pyd to the support through an O-linked bond.

As explained above, the acylating agent used in forming the functionalized Pyd may be a protected sulfhydryl group, which is then deprotected, after coupling to Pyd, to produce a thiolated pyridinoline. The thiolated pyridinoline is then reacted with a maleimide group immobilized on the solid support. The O-derivatized Pyd on the solid support has accessible pyridinium and peptide moieties, and a uniform structural attachment to the support.

VI.C. Calibration of Immunoassay

The solid-phase immunoassay for detection of Pyd, described above, utilizes a solid-phase reagent having an O-linked Pyd, and an antibody preferably prepared using the Pyd immunogen of the invention. In a typical assay format, a Pyd-containing sample, which may be hydrolysed, is mixed with an anti-Pyd antibody in the presence of the solid support. The sample Pyd competes with the solid-phase Pyd for binding to the solid support, to attach the antibody to the support in inverse proportion to the amount of Pyd in the sample.

It is necessary, in carrying out the assay, to establish a standard curve of Pyd concentration vs. signal measured on the solid support. In this aspect of the invention, the standard curve is generated by an acylated pyridinoline of the invention, e.g., Ac-Pyd. Here calibration samples containing increasing known concentrations of the acylated Pyd are reacted in the assay method, and the signal recorded for the solid-phase bound material is plotted against the known concentrations of calibrant. The standard curve so generated is then used for determining Pyd concentrations in samples, according to the measured solid-phase signal. This approach is detailed in Example 9.

Figure 12:
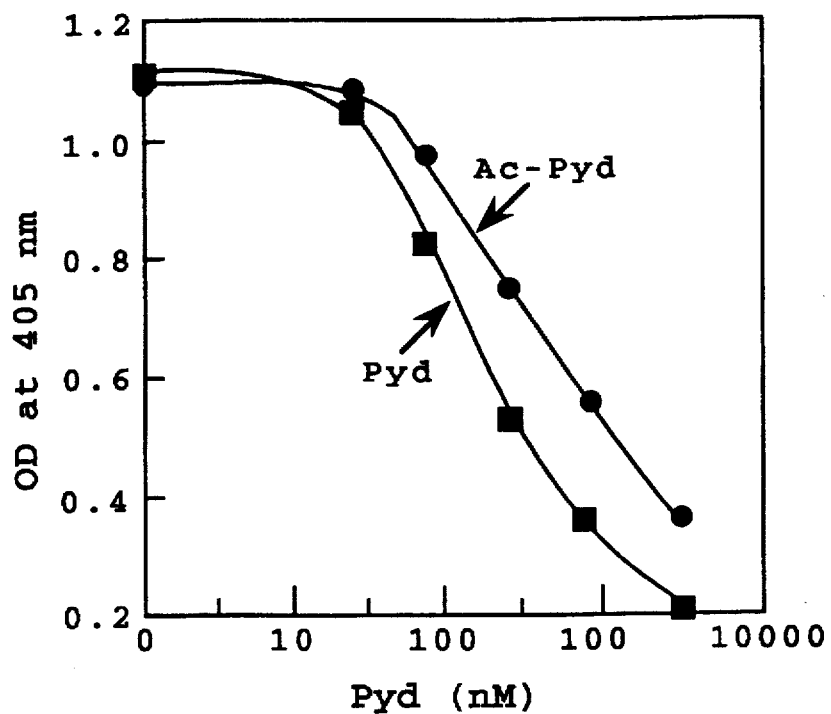
FIG. 12 shows standard curves for Pyd and Ac-Pyd in an immunoassay using anti-Pyd antibodies. The assay involved a competitive format in which Pyd had been immobilized on a solid support via the amino groups of Pyd, and in which standard Pyd or Ac-Pyd competed with the immobilized Pyd for soluble anti-Pyd antibodies.

FIG. 12 shows calibration curves for Pyd and Ac-Pyd constructed as indicated above. The curves show the relationship between a given Ac-Pyd amount, as measured in the immunoassay, and the same amount (concentration) of free Pyd. The two, in other words, indicate how a standard curve generated for Ac-Pyd can be corrected for determining Pyd in an assay. It is noted that a sample, such as a urine sample, may be pretreated, for example by passage through a nitrocellulose membrane, prior to its reaction with the solid-phase reagent. In this case, it is recommended that the Ac-Pyd calibrations are taken through the same pretreatment procedures.

The following examples illustrate, but in no way are intended to limit the scope of the invention.

EXAMPLES

Materials and Methods

All chemicals and solvents were of analytical or HPLC grade and were obtained either from the sources listed below, or from other sources that provided reagents of comparably high purity. Anhydrous trifluoroacetic acid (TFA, in 1 mL sealed ampules) and acetonitrile were from J. T. Baker; acetyl chloride was from Aldrich (Milwaukee, Wis.); dimethylformamide (silylation grade, sealed under $N_2$) and heptaf luorobutyric acid (HFBA) in 1 mL sealed ampules was from Pierce (Rockford, Ill.). Acetic acid (glacial) was from Fisher Scientific. Distilled, deionized water was used for HPLC, and all HPLC solvents were filtered through 0.22 micron filters (Millipore type GV, Bedford, Mass.). Microgranular and fibrous cellulose powders (CC31 and CF1, respectively) were obtained from Whatman, Inc.

Preparation of Pyd

Hydrolyzed Pyd was isolated from hydrolyzed powdered bovine or sheep bone as described by Black et al. (1988).

Native Pyd was isolated from un-hydrolyzed urine as follows. Human urine was filtered through a 3000 kD cut-off filter (Filton Co.) applying 40 psi of back pressure. The filtrate was then lyophilized and reconstituted to 1/20 of the original volume with 0.2M acetic acid.

Concentrated urine was then applied onto a Sephadex G-10 2.6×95 cm column equilibrated with 0.2M acetic acid. Elution from the column material was analyzed for free Pyd and Dpd as described above (HPLC protocol C). The free crosslink containing fractions were pooled together, adjusted to pH 2.0 and applied onto 1×18 cm cation exchange column (Locarte Co., UK) and equilibrated with 0.1M sodium citrate pH 4.2.

Glyco-Pyd, Pyd and Dpd were coeluted thereafter from the ion exchange column with 0.1M sodium citrate pH 4.2. Collected fractions were analyzed for the presence of crosslinks by HPLC analysis as above. Fractions containing crosslinks Glyco-Pyd, Pyd, and Dpd were pooled together and applied onto 10×2.5 cm reversed phase C18 column (Waters) which was subsequently developed with 2-20% gradient of acetonitrile containing 0.1% HFBA. Separated species (glyco-Pyd, Pyd and Dpd) were collected and concentrated by lyophilization. The dry residues were reconstituted in 0.2M acetic acid and stored at 4° C. Purity of isolated Pyd was measured by gravimetric and elemental analysis, and was found to be greater than 97%.

High Performance Liquid Chromatography (HPLC)

A. Analytical HPLC

Analytical HPLC was performed using one of three protocols (A, B, and C). Samples were typically diluted with 1-3% HFBA prior being loaded on the HPLC column.

In protocol A, for analysis of purified Pyd, Dpd, and products of acylation reactions, the HPLC system included a Hewlett Packard Series 1050 injector and pump system linked to a Shimadzu RF 551 fluorescence monitor, set at 295 nm excitation and 395 nm emission, a Beckman (Fullerton, Calif.) System Gold analog interface system, a Microsorb C18 "Short-One" reversed phase column (100× 4.6 mm, Rainin Instrument Co., Inc., Woburn, Mass.), and a 20×2 mm guard column containing C18 packing between two 0.5 µm frits. The solvent system consisted of 12% acetonitrile/0.1% HFBA in water at a flow rate of 1.00 mL/min. The column and tubing leading to the fluorimeter were maintained at a constant temperature (30° C.) via containment in a temperature control chamber to minimize changes in fluorescence yield due to fluctuations in ambient temperature (Black et al., 1988).

In protocol B, for analysis of hydrolyzed urine samples, the HPLC system consisted of a Hewlett Packard 1050 HPLC equipped with pumps, fluorescence detector, and accompanying software. The column, identical in type to that in protocol A, and tubing were maintained at 30° C. as above. The elution gradient was as follows: isocratic elution at 3% B for two minutes, linear gradient from 3% to 16% B over 1 minute, linear gradient from 16% to 21% B for 8 minutes (separation gradient), linear gradient from 21% back to 3% B over 2 minutes, and equilibration at 3% B for 7 minutes; flow rate=1 ml/min; A=0.3% HFBA in water, B=0.3% HFBA in 75% acetonitrile. For routine processing of urine samples, the HPLC system was linked directly to an automated liquid handling robotic station (ASPEC), described in Example 5.

In protocol C, for analysis of hydrolyzed or un-hydrolyzed urine samples, the gradient HPLC system included two Gilson 302 pumps, a Shimadzu RF-530 fluorescence monitor (Ex. 295 nm, Em. 400 nm), an Apple IIe controller, and a Microsorb C18 Short-One column plus guard column as in protocol A. An in-line stainless steel coil (0.4 mm i.d.; 100 µl) immersed in a constant temperature bath (10° C.) was included immediately before the fluorimeter to avoid the variations in fluorescence yield noted in protocol A. A two-stage gradient was used: linear gradient from 17% to 20% B over first 7 minutes, linear gradient from 20% to 25% over next 5 minutes, maintain 25% B for 2 minutes, raise sharply to and maintain at 70% B for 6 minutes to remove residual contaminants, and equilibrate at 17% B for several minutes to return to initial conditions; flow rate=1 ml/min; A=10 mM HFBA in water, B=10 mM HFBA in 75% acetonitrile.

B. Preparative HPLC

Preparative HPLC (Protocol D) was performed using a Beckman System Gold interface equipped with a Programmable Solvent Module 126, and a Waters (Milford, Mass.) Nova-Pak HR C18 reversed phase column (100×25 mm). An elution gradient of 2%-40% acetonitrile in aqueous 0.1% HFBA at 10 mL/min over 60 min was used. Fractions (5 mL) were collected every 0.5 min using a Bio-Rad (Richmond, Calif.) Model 2100 fraction collector. Use of this method is described in Example 2.

EXAMPLE 1

Small-Scale Preparation of O-Acetylated and O-Propionylated Pyd

O-acetylated (Ac-Pyd) and O-propionylated (Pr-Pyd) forms of Pyd were prepared on a small scale from the corresponding acid chlorides. Dry Pyd (e.g. 2.5 nmol) in a polypropylene micro-reaction vial was dissolved in 0.3 ml of a trifluoroacetic acid/acid chloride mixture (9:1 v/v, prepared immediately before use). The vial was capped, mixed, and incubated for 60 minutes at 20° C. The reaction was stopped by mixing with a drop of water, and the solution was taken to dryness in a centrifugal evaporator. Typical yields were in the range of 47–76%. Alterations in temperature and time of reaction did not appear to improve the yield, and the presence of moisture or salts were found to diminish the yield.

To compare the elution properties of Ac-Pyd and Pr-Pyd with Pyd, acylation reactions were carried out with acetyl chloride and propionyl chloride as in the preceding paragraph, except that the reactions were stopped by addition of water after 15 minutes so that a substantial amount of unreacted Pyd remained. After the reaction mixtures were evaporated to dryness, the reaction products were dissolved in 1 ml of water, and aliquots were diluted in 1% (w/v) HFBA for HPLC analysis (protocol C).

Elution profiles of the reaction products are shown in FIG. 2, where peak 1 is Pyd, peak 2 is Ac-Pyd, and peak 3 is Pr-Pyd. As can be seen, both acylated products eluted after Pyd, with Ac-Pyd eluting about 2 minutes (upper trace), and Pr-Pyd about 4.5 minutes (lower trace), later than Pyd.

EXAMPLE 2

Large Scale Preparation of O-Acetylated Pyd

Acetylation of Pyd was performed by reacting purified Pyd with acetyl chloride in anhydrous trifluoroacetic acid, following the acylation method of Previero et al. (1972).

To a thoroughly dried sample of Pyd (10 mg, 0.023 mmol) in a glass screw-cap vial was added a premixed solution of 9.0 mL anhydrous trifluoracetic acid and 1.0 mL acetyl chloride. The reaction vial was capped with an air-tight screw-cap teflon seal and allowed to react with stirring at room temperature for 20 min (in contrast to the 60 minutes used in Example 1, a shortened reaction time was sufficient here, possibly because of the much higher concentration of Pyd in these conditions). The reaction was quenched by adding eight drops of water over 15 min. The solvent was evaporated using a vigorous stream of Ar gas followed by further evaporation in a centrifugal evaporator to yield a brown resinous solid. The resinous solid was then dissolved in 200 µl dry DMF, followed by the addition of 1.8 mL of 2% HFBA (2.0 ml final volume). HPLC analysis (protocol A) of an aliquot of the mixture revealed the elution profile summarized below:

| Elution time (min) | identity | % total integration |
| --- | --- | --- |
| 7.38 | unknown | 3.6% |
| 7.65 | Pyd | 10.7% |
| 8.50 | AcPyd | 81.4% |
| 10.26 | unknown | 1.2% |
| 11.75 | unknown | 2.3% |
| 13.97 | unknown | 0.7% |

The product mixture was purified preparatively by HPLC (protocol D). Monitoring the effluent at 296 nm (UV-visible absorbance) revealed a single major peak (fractions ~40–65), of which fractions 44–62 were found to contain AcPyd of at least 98% purity, as judged by analytical HPLC of individual fractions. Fractions 44–62 were pooled, freeze dried, and the resultant white powder was stored at 4° C. Yield: ~45–65%.

As an alternative method, purification of Ac-Pyd could be carried out using a Locarte amino acid analyser (160×9 mm column). Separation of Ac-Pyd from unreacted Pyd was performed using 68 mM tri-sodium citrate, pH 4.25, at 55° C. Fractions containing purified Ac-Pyd were pooled and stored at −20° C.

Both this method and the preparative HPLC method described above provided Ac-Pyd of about the same purity (typically >97% pure). The fluorescence yield of Ac-Pyd was found to be the same as that of Pyd.

EXAMPLE 3

Structural Characterization of O-Acetylated Pyd

To determine what group(s) on Pyd had been acylated in the reaction conditions described in Examples 1 and 2, acetylated Pyd prepared as in Example 2 was characterized by UV-visible and $^1$H-NMR spectroscopies.

To determine whether the ring hydroxyl group had been acetylated, acetylated Pyd produced as in Example 1 was examined by UV-visible spectroscopy under acidic and neutral pH conditions. Spectra were recorded in the range of 200–500 nm using an HP 8452A diode array spectrophotometer.

Approximately 12 µg of acetylated Pyd were dissolved in 750 µl of 0.01M HCl (final pH~3). The mixture was placed in a 1 cm pathlength cuvette, and the UV-vis spectrum was recorded. In the wavelength range of 260–360 nm, a single peak was observed ($\lambda$max=294 nm, 0.44 AU). HPLC analysis of an aliquot of this solution dissolved in 2% HFBA showed that no hydrolysis of the acetyl group had occurred. The pH of the cuvette solution was then adjusted to about 7 by addition of 1M NaHCO$_3$, and the spectrum was recorded again. The peak at 294 nm was now absent, and a new peak at 326 nm was observed (0.38 AU). This result indicated that the ring hydroxyl group of Ac-Pyd was not acetylated.

To further characterize the chemical structure of Ac-Pyd, dried samples of Pyd and Ac-Pyd (~3 mg each) were submitted for $^1$H NMR analysis to the National Center for NMR Applications at the Department of Chemistry, Colorado State University, Fort Collins, Col. High field $^1$H NMR spectra were recorded on Bruker AM-500 (for Pyd, 500 MHz) and AM-600 (for Ac-Pyd, 600 MHz) FT spectrometers. A water-suppression sequence was used in data collection for Pyd only, and proton decoupling was used to help identify some of the peaks. The spectra obtained are summarized in Table 1, with shift values listed in ppm downfield from an external standard (DSS) in deuterium oxide.

EXAMPLE 4

HPLC of Ac-Pyd and Pr-Pyd in the Presence of Fluorescent Urinary Components

To investigate the suitability of Ac-Pyd and Pr-Pyd for use as standards for the quantitation of urinary Pyd and Dpd by HPLC, small amounts of Ac-Pyd and Pr-Pyd were added to aliquots of a sample of pre-fractionated, unhydrolyzed urine, and each mixture was analyzed by HPLC (Protocol C).

The resulting chromatograms for urine sample alone (trace A), urine sample plus Ac-Pyd (trace B), and urine sample plus Pr-Pyd (trace C), are shown in FIG. 5. Note that peak 1 is glycosylated Pyd, peak 2 is Pyd, peak 3 is Dpd, peak 4 is Ac-Pyd, and peak 5 is Pr-Pyd. The Figure shows that under these conditions, Ac-Pyd is a more suitable standard than Pr-Pyd, since the former elutes in a region that is vacant for the unhydrolyzed urine sample alone, whereas the latter coelutes with an unknown peak present in the urine sample.

EXAMPLE 5

Quantitation of Pyd Using an Automated HPLC Procedure With O-Acetylated Pyd as an Internal Standard For this study, an ASPEC™ liquid handling robotic station (Gilson, France) was used to facilitate the extraction of hydrolyzed crosslinks from urine samples. The ASPEC was equipped with individual 1 ml disposable extraction columns (Analytichem International, Inc., Harbor City, Calif.), each containing 100 mg of CC31 microgranular cellulose powder bordered in the column by two polyethylene frits (20 µm pore size). For each sample, the ASPEC was able to add solvents to the sample, load the sample onto an extraction column, treat the column with a solvent sequence to elute hydrolyzed crosslinks, and load the collected crosslinks onto a reversed phase C18 HPLC column for analysis (protocol B or C).

Hydrolyses of urine samples were carried out by mixing 1 ml of a urine sample with 1 ml of 12N HCl and heating the mixture for 18 hours at 110° C. in a tightly sealed vial. Following hydrolysis, the samples were allowed to settle by gravity or were centrifuged at 13,500×g for 2 min. Aliquots of the supernatants (0.6 ml) were added to 10×75 mm glass tubes in the sample rack of the ASPEC™. The ASPEC was also loaded with an extraction column for each sample tube. The ASPEC dilutor reservoir was filled with mobile phase (1-butanol:acetic acid:water, 4:1:1 v/v/v), and the solvent rack was loaded with separate bottles of Ac-Pyd standard (200 nM Ac-Pyd in 90% acetic acid), butanol, DMF, and 1% HFBA (for sample dilution). The ASPEC was programmed to perform the following steps:

1. Condition column with 1 ml of mobile phase.
2. Add to the sample tube 0.6 ml of Ac-Pyd standard and 2.4 ml n-butanol, and mix mixture (3.6 ml) by sparging.
3. Load sample mixture onto column.
4. Wash column with 4 ml of mobile phase (8 ml for concentrated urine samples).
5. Wash column with 1.5 ml of DMF.
6. Dry column with 3 ml air.
7. Elute crosslinks with 0.6 ml of 1% HFBA.
8. Dry column with 1.5 ml air.

The flow rates for the above steps were adjusted to avoid high back-pressure, and were generally in the range of 0.5–1.5 ml/min.

The presence of butanol in the eluted crosslinks caused severe peak broadening and loss of peak retention in subsequent reversed phase HPLC analysis. Accordingly, a wash step using DMF (step 5) was included to remove residual butanol from the column prior to elution of the crosslinks with 1% HFBA. A drying step (step 6) was also included to wash the DMF from the column.

Figure 4:
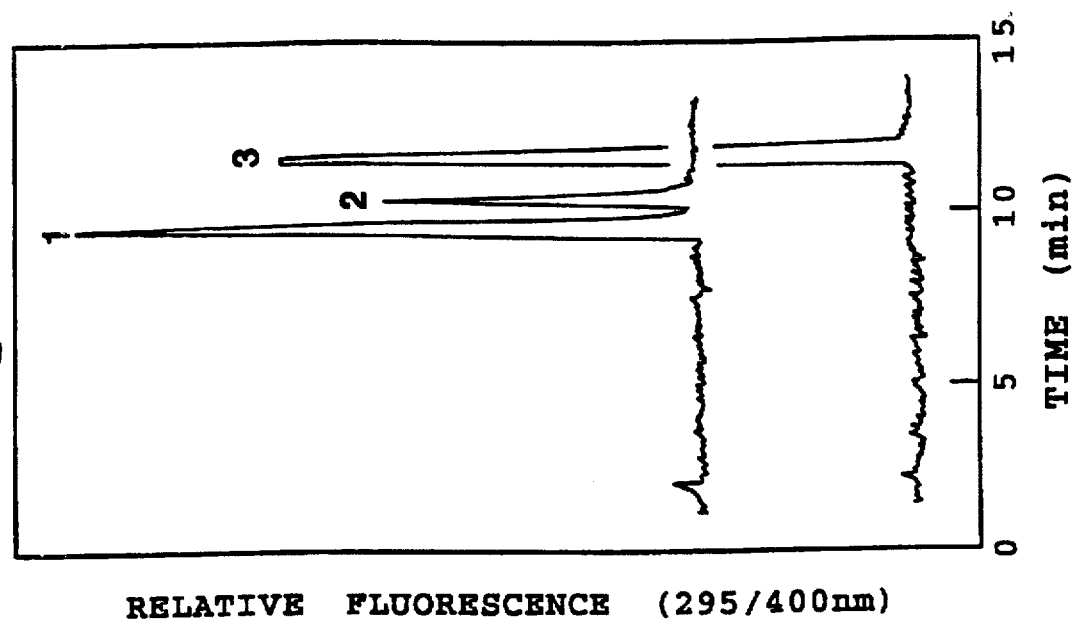
FIG. 4 shows reversed phase C18 HPLC chromatograms of a mixture of Pyd and Dpd (upper trace) and of purified Ac-Pyd (lower trace) prepared by a method of the present invention. Peak identification: 1, Pyd; 2, Dpd; 3, Ac-Pyd.

Following dilution in 2% HFBA, extracted crosslink samples were chromatographed as in protocol B. For quantitation of Pyd and Dpd in the urine samples, the fluorescence peak integrator was calibrated for internal standardization using peak areas obtained from a standard mixture analyzed by the HPLC at the beginning of each batch of samples, thereby establishing a response factor correlating peak area with loaded amount of Pyd and Dpd. The standard mixture contained 120 nM Pyd and 40 nM Dpd in water. The Pyd and Dpd contents of a urine sample were determined automatically based on peak integration using the formula:

$$\text{content} = \frac{RF \times \text{Peak Area}}{\text{Area of IS Peak}} \times \frac{IS \text{ Weight}}{\text{Sample Dilution}}$$

where RF is the response factor determined from the Pyd/Dpd standard mixture, Peak Area is the peak area measured for the Dpd or Pyd from the urine sample, IS Peak is the peak for the Ac-Pyd internal standard that had been added to the urine sample in step 2 of the ASPEC cellulose chromatography procedure, IS weight is the amount of Ac-Pyd added to the sample in step 2, and Sample Dilution is the amount by which the extracted sample was diluted prior to loading on the HPLC column. FIG. 4 illustrates the purity, as measured using HPLC protocol C, of the Pyd/Dpd standard mixture used to calibrate detector response (upper trace) and of the Ac-Pyd internal standard used to quantitate crosslink recovery (lower trace).

A chromatogram of a typical hydrolyzed urine sample extracted and analyzed as above is shown in FIG. 6A.

EXAMPLE 6

Analysis of Samples Having High Creatinine Levels

The automated HPLC procedure of Example 5 was used to process and analyze hydrolyzed urine samples having high creatinine concentrations. DMF, THF, ethanol and acetone were each tested as the wash solvent in step 5 of the extraction procedure. All four solvents produced improved peak shape and retention in comparison to what was obtained when the wash step was omitted, with DMF and THF providing the best results.

FIGS. 6B and 6C show HPLC chromatograms of a urine sample having a high creatinine level (25 mM), where THF (FIG. 6B) or DMF (FIG. 6C) was used in step 5. As can be seen, the resolution of peaks was good despite the high concentration of creatinine originally present in the sample. Moreover, the crosslink mixture afforded by DMF was significantly cleaner than the mixture afforded by THF.

EXAMPLE 7

Crosslink Levels Measured With and Without Ac-Pyd Internal Standard

To characterize the effectiveness of Ac-Pyd as an internal standard for quantitating the recovery of the crosslinks, five aliquots of a hydrolyzed urine sample containing a known concentration of Pyd were spiked with additional amounts of Pyd, yielding final Pyd concentrations: 905, 1275, 1650, 1943, and 2141 nM. The spiked samples were then extracted by cellulose chromatography and analyzed by reversed phase HPLC, by the general procedure described in Example 5. As a control, the spiked samples were also analyzed by HPLC without performing the extraction procedure.

Figure 7:
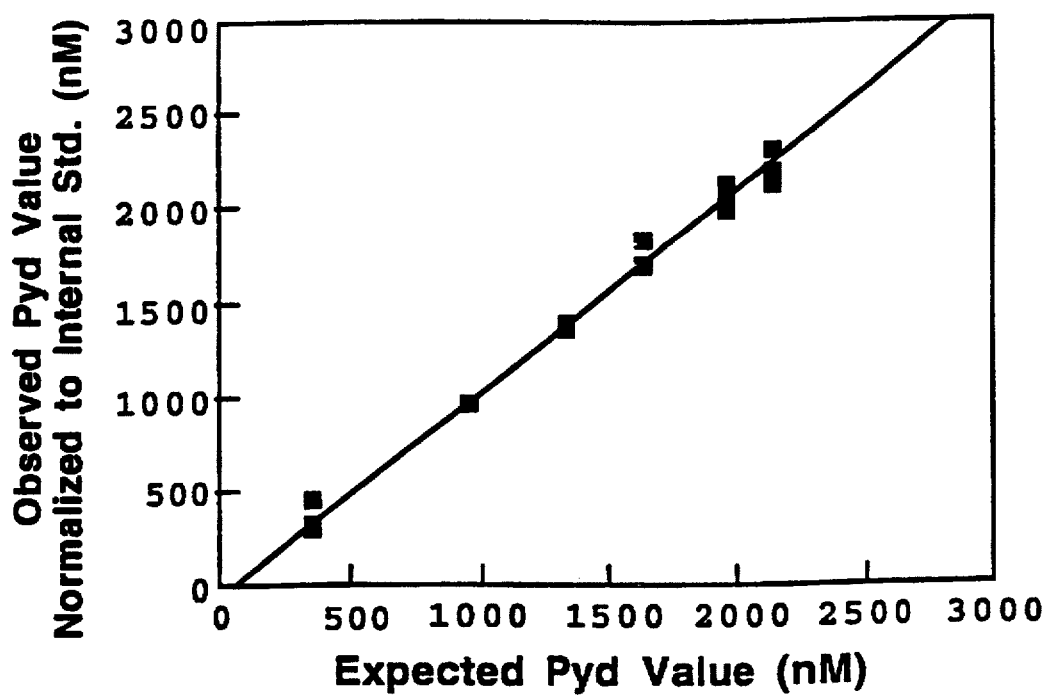
FIG. 7 shows a correlation between expected and observed levels of pyridinoline in a urine sample based on added Ac-Pyd as a standard in an HPLC assay.

In general, the observed levels (uncorrected) of Pyd from the extracted samples were found to be about 80–82% of those originally loaded. Correction of these levels using the integrated peak area for Ac-Pyd by the method outlined in Example 5 afforded corrected Pyd levels that were close (~100%) to those originally present prior to the cellulose extraction step. The good agreement of expected and observed (corrected) values of Pyd is shown in FIG. 7; the slope of the line was 1.07, and the correlation coefficient was 0.997.

EXAMPLE 8

Stability of Ac-Pyd in a Storage Solution

Since hydrolyzed urine samples are typically mixed with butanol and acetic acid (final ratio butanol:acetic acid- :sample≈4:1:1 v/v/v) for cellulose chromatography, different solvent conditions were investigated to develop an Ac-Pyd standard solution that would be stable as well as convenient to use. The most convenient approach appeared to be to include the Ac-Pyd standard in the acetic acid reagent added to the urine sample. However, monitoring of Ac-Pyd in acetic acid showed that about 20% of Ac-Pyd was lost after about 4 days. This loss was not accompanied by an increase of free Pyd. Since acetic anhydride is a known trace contaminant in even the purest grades of acetic acid, the involvement of acetic anhydride in the loss of Ac-Pyd was tested by preparing solutions of Ac-Pyd (120 nM) in (A) acetic acid, (B) acetic acid containing 0.1% added acetic anhydride, (C) 90% acetic acid in water additionally containing 0.1% acetic anhydride (D) 90% acetic acid in water (no acetic anhydride added). To follow the disappearance of Ac-Pyd, aliquots were removed periodically and analyzed by HPLC (protocol C). The results are shown in FIG. 8.

Trace A shows the rate of loss of Ac-Pyd in acetic acid alone. To investigate whether this loss could be the result of trace amounts of acetic anhydride in the sample, acetic anhydride was added to a final concentration of 0.1%. As seen from trace B, the added acetic anhydride markedly increased the rate of loss of Ac-Pyd, such that virtually none remained after 4 days (trace B). The effect of added acetic anhydride could be substantially reduced by the inclusion of water (10% final concentration, trace C). When the solvent was 90% acetic acid in water (no added acetic anhydride), no detectable loss of Ac-Pyd had occurred after 5 days (trace D), showing that the trace contaminant (presumably acetic anhydride) in the acetic acid had been effectively inactivated by the addition of water. Accordingly, the last conditions 90% acetic acid in water) were selected for the internal standard solution.

EXAMPLE 9

Use of O-Acetylated Pyd as a Calibrant in an Immunoassay for Pyd

To test Ac-Pyd as a possible calibrant in an immunoassay for quantitating N Pyd, the relative affinities of Pyd and Ac-Pyd for an anti-N-Pyd antibody were measured using a competitive immunoassay format in which Pyd has been immobilized on a solid support. The assay is available in kit form (the Crosslinks™ assay) from Metra Biosystems, Palo Alto, Calif.

Solutions of purified Pyd and Ac-Pyd in 0.1M phosphate buffer, pH 7, were prepared with the following concentrations: 0, 25, 75, 250, 750, 3000 nM. A molar extinction coefficient of 5420 AU/cm-M at 326 nm was used in measuring concentrations of both compounds. Aliquots (10 ul) of each solution were pipetted into microtiter plate wells (3 replicates) coated with a Pyd-bovine serum albumin conjugate, followed by the addition of 150 ul of PBS solution containing a predetermined amount of rabbit anti-N-Pyd antiserum. The resultant reaction mixtures were incubated for 18 hours at 4° C., after which the wells were washed with PBS (3×250 ul) to remove unbound antibodies. The antibodies bound to the solid support were then developed by incubating the wells for 1 hour at room temperature with 150 ul of a solution containing alkaline phosphatase-labeled goat-anti-rabbit immunoglobulin conjugate solution. After removal of unbound conjugate with PBS, the wells were incubated at room temperature for 1 hour with 150 ul of p-nitrophenylphosphate (2 mg/mL) in 1M diethanolamine containing 1 MM $MgCl_2$, pH 9.8. After the 1 hour period, the extent of reaction of p-nitrophenylphosphate in each well was measured by absorbance at 405 nm.

Representative calibration curves for Pyd and Ac-Pyd assay are shown in FIG. 12. Although the anti-Pyd antibody did not bind Ac-Pyd as strongly as Pyd, the Figure shows how a calibration curve based on Ac-Pyd as a standard can be used to determine the concentration of Pyd from a urine sample. Specifically, with reference to FIG. 12, an observed absorbance of about 0.55 OD corresponds to about 900 nM Ac-Pyd, and to about 500 nM Pyd.

Although the invention has been described with respect to particular embodiments, it will be appreciated that various changes and modifications can be made without departing from the invention.

It is claimed:

1. A pyridinoline-protein conjugate having the following structure:

```
                        CH₂CHNH₂COOH
HOOCH₂NCHCH₂CH₂    4
                  5      OH
                      3
                      2
                   N₁
                   |
                   CH₂
                   |
                   CH-L-Prot
                   |
                   CH₂
                   |
                   CH₂
                   |
                   CHNH₂COOH
``` wherein Prot is a carrier protein, L is a linker, and said pyridinoline-protein conjugate is effective to serve as an immunogen for raising an antibody specific for the pyridinoline moiety in the conjugate.

2. The conjugate of claim 1, having the following structure:

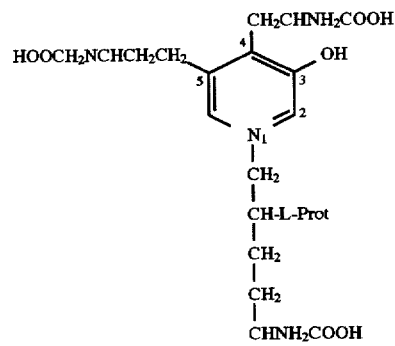

wherein Pyd represents the pyridinoline moiety in the conjugate.

3. The conjugate of claim 1, having the following structure:

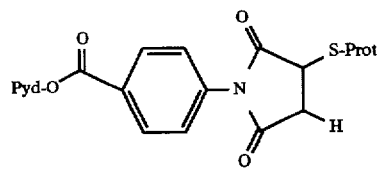

wherein Pyd represents the pyridinoline moiety in the conjugate.

4. The conjugate of claim 1, having the following structure:

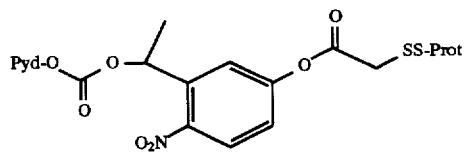

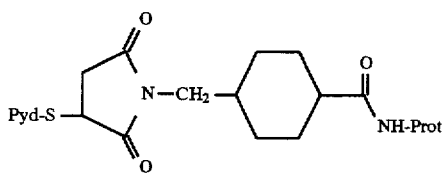

wherein Pyd represents the pyridinoline moiety in the conjugate.

5. The conjugate of claim 1, wherein Prot is keyhole limpet hemocyanin or bovine serum albumin.

6. The conjugate of claim 5, having the following structure:

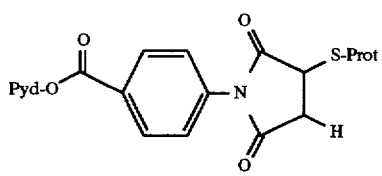

wherein Pyd represents the pyridinoline moiety in the conjugate.

7. The conjugate of claim 5, having the following structure:

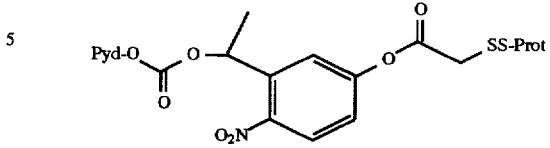

wherein Pyd represents the pyridinoline moiety in the conjugate.

8. The conjugate of claim 5, having the following structure:

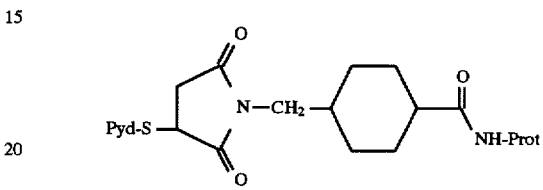

wherein Pyd represents the pyridinoline moiety in the conjugate.

* * * * *